(12) United States Patent
Hollebeek et al.

(10) Patent No.: US 10,471,279 B2
(45) Date of Patent: Nov. 12, 2019

(54) PROTON DOSE IMAGING METHOD AND APPARATUS

(71) Applicant: The Trustees of the University of Pennsylvania, Philadelphia, PA (US)

(72) Inventors: Robert Hollebeek, Berwyn, PA (US); Derek Dolney, Huntingdon Valley, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 14/453,292

(22) Filed: Aug. 6, 2014

(65) Prior Publication Data
US 2015/0041665 A1  Feb. 12, 2015

Related U.S. Application Data
(60) Provisional application No. 61/862,683, filed on Aug. 6, 2013.

(51) Int. Cl.
*A61N 5/10* (2006.01)
*G01T 1/29* (2006.01)

(52) U.S. Cl.
CPC .......... *A61N 5/1071* (2013.01); *G01T 1/2935* (2013.01); *A61N 2005/1087* (2013.01)

(58) Field of Classification Search
CPC .................. G01T 1/185; G01T 1/2935; A61N 2005/1087; A61N 5/1071
See application file for complete search history.

(56) References Cited

U.S. PATENT DOCUMENTS

| | | | |
|---|---|---|---|
| 5,038,043 A * | 8/1991 | Dorion et al. | 250/374 |
| 5,308,987 A * | 5/1994 | Wuest et al. | 250/374 |
| 6,133,575 A | 10/2000 | Charpak et al. | |
| 6,362,484 B1 * | 3/2002 | Beyne et al. | 250/374 |
| 7,411,198 B1 * | 8/2008 | Holland | G06G 7/18 250/370.01 |
| 2003/0212325 A1 * | 11/2003 | Cotrutz | A61N 5/1031 600/436 |
| 2005/0205796 A1 * | 9/2005 | Bryman | 250/370.11 |
| 2006/0049362 A1 * | 3/2006 | Friedman et al. | 250/374 |

(Continued)

FOREIGN PATENT DOCUMENTS

WO  WO 2013/029748  3/2013

OTHER PUBLICATIONS

Kim, Jong-Won, et al., "Development of dosimetry tools for proton therapy research," Radiation Measurements, 45, 2010, 1417-1421.

(Continued)

*Primary Examiner* — Nicole M Ippolito
*Assistant Examiner* — Sean M Luck
(74) *Attorney, Agent, or Firm* — BakerHostetler

(57) ABSTRACT

Particle therapy systems and methods for particle dose imaging are provided. A particle therapy system includes a particle beam source for generating a particle beam; and at least one particle detector including an ionization chamber having a mesh electrode. The at least one particle detector is configured to receive the particle beam and to generate an ionization current responsive to the received particle beam. The ionization current may be used to characterize the particle beam.

20 Claims, 22 Drawing Sheets

(56) References Cited

U.S. PATENT DOCUMENTS

| | | | |
|---|---|---|---|
| 2006/0138340 A1* | 6/2006 | Ianakiev | G01T 3/008 250/390.01 |
| 2008/0023644 A1* | 1/2008 | Pedroni | A61N 5/10 250/400 |
| 2008/0029709 A1* | 2/2008 | Yeo | A61N 5/1048 250/374 |
| 2008/0251732 A1* | 10/2008 | Dick et al. | 250/382 |
| 2009/0039249 A1* | 2/2009 | Wang | G01N 15/0205 250/287 |
| 2009/0084972 A1* | 4/2009 | Tamagawa et al. | 250/374 |
| 2009/0175412 A1* | 7/2009 | Grodzins | G01N 23/04 378/57 |
| 2010/0228116 A1 | 9/2010 | Lu et al. | |
| 2010/0265078 A1* | 10/2010 | Friedman | 340/600 |
| 2011/0211675 A1* | 9/2011 | Ramsden | G01T 1/40 378/82 |
| 2011/0272591 A1* | 11/2011 | De Oliveira | 250/385.1 |
| 2011/0309261 A1* | 12/2011 | Friedman et al. | 250/382 |
| 2012/0140887 A1* | 6/2012 | Mundy | A61N 5/1048 378/65 |
| 2012/0305793 A1* | 12/2012 | Schiefer | A61N 5/1048 250/394 |

OTHER PUBLICATIONS

Kurosawa S., et al., "Prompt Gamma Detection for Range Verification in Proton Therapy," Current Applied Physics 12 (2012), 364-368.

Agostinelli, S., et al., "GEANT4—a Simulation Toolkit," Nuclear Instruments and Methods in Physic Research A 506 (2003), 250-303.

Arjomandy, B., et al., "Use of Two-Dimensional Ionization Chamber Array for Proton Therapy Beam Quality Assurance," Med. Phys. 35 (9), Sep. 2008, 3889-3894.

Beddar S., et al., "Exploration of the Potential of Liquid Scintillators for real-Time 3D Dosimetry of Intensity Modulated Proton Beams," Med. Phys. 36 (5), May 2009, 1736-1743.

Boon, S.N., et al., "Performance of a Fluorescent Screen and CCD Camera as a Two-Dimensional Dosimetry System for Dynamic Treatment Techniques," Med. Phys. 27 (10), Oct. 2000, 2198-2208.

Giomataris, Y., "Development and Prospects of the New Gaseous Detector 'Micromegas'," Nuclear Instruments and Methods in Physics Research A 419 (1998), 239-250.

Giomataris, Y., "Micromegas: a high-granularity position-sensitive gaseous detector for high particle-flux environments," Nuclear Instruments and Methods in Physics Research A 376 (1996), 29-35.

Giomataris, I., et al., "Micromegas in a Bulk," Nuclear Instruments and Methods in Physics Research A 560 (2006) 405-408.

Giomataris, I., "High Rate Applications of Micromegas and Prospects," SNIC Symposium, Stanford, California—Apr. 3-6, 2006, 1-5.

Gottschalk, B., et al., "Water Equivalent Path Length Measurement in Proton Radiotherapy Using Time Resolved Diode Dosimetry," Med. Phys. 38 (4), Apr. 2011,2282-2288.

Halbach, K., et al., "Superfish—A Computer Program for Evaluation of RF Cavities with Cylindrical Symmetry," Particle Accelerators, 1976, vol. 7, 213-222.

Hartmann, B., et al., "Investigations of a Flat-Panel Detector for Quality Assurance Measurements in Ion Beam Therapy," Phys. Med. Biol. 57 (2012) 51-68.

Jarlskog, C., et al., "Physics Settings for Using the Geant4 Toolkit in Proton Therapy," IEEE Transactions on Nuclear Science, vol. 55, No. 3, Jun. 2008, 1018-1025.

Johnson, L., et al., "Initial Studies on Proton Computed Tomography Using a Silicon Strip Detector telescope," Nuclear Instruments and Methods in Physics Research A 514 (2003), 215-223.

Lu, H., "A Point Dose Method for In Vivo Range verification in Proton Therapy," Phys. Med. Biol, 53 (2008), N415-N422.

Mumot, M., et al., "Proton Range Verification Using a Range Probe: Definition of Concept and Initial Analysis," Phys. Med. Biol. 55 (2010), 4771-4782.

Oliviera, R., et al., "First Tests of Micromegas and GEM-Like Detectors Made of a Resistive Mesh," IEEE Transactions on Nuclear Science, vol. 57, No. 6, Dec. 2010, 3744-3752.

Penfold, S.N., et al., "Geometrical Optimization of a Particle Tracking System for Proton Computed Tomography," Radiation Measurements 46 (2011), 2069-2072.

Schneider, U., et al., "First Proton Radiography of an Animal Patient," Med Phys. 31 (5), May 2004, 1046-1051.

Schulte, R., et al. "Conceptual Design of a Proton Computed Tomography System for Applications in Proton Radiation Therapy," IEEE Transactions on Nuclear Science, vol. 51, No. 3, Jun. 2004, 866-872.

Smith, A., "Vision 20/20: Proton Therapy," Med. Phys. 36(2), Feb. 2009, 556-568.

Titov, M., "New Developments and Future Perspectives of Gaseous Detector's," Nuclear Instruments and Methods in Physics research A 581 (2007), 25-37.

http://geant4.web.cer.ch/geant4/results/validation%5C_plot/cross%5C_sections/hadrinic/inelastic/test1/inelastic.shtml, Mar. 7, 2007, 5 pages.

Jermann, M., 2012, http://ptcog.web.psi.ch/ptcentres.html, Mar. 2013.

Ainsley, C., et al., "Design and Performance of a Multileaf Collimator for Proton Therapy," In 48$^{th}$ Meeting of the Particle Therapy Co-Operative Group, 2009, Abstract.

Ainsley, C., et al., "Monte Carlo Simulation and Development of a Multileaf Collimator for Proton Therapy," Med. Phys., 36(6):2702, 2009. Abstract for AAPM 51$^{st}$ Annual Meeting.

Andreo, P., "Monte Carlo Techniques in Medical Radiation Physics," Phys. Med. Biol., 36, 1991, 861-920.

Avery, S., et al., "Analytical Shielding Calculations for a Proton Therapy Facility," Radiat. Prot. Dosimetry , 131 (2), 2008, 167-179.

Barrillon, P., et al., "Integrated Electronic for SiPM and MPPCs," International Workshop on Photon Detectors PD07, 2007, 1-19.

Both, S., et al., "An Independent Program for MU Check of Modulated Scanning Beam for IMPT," Med. Phys., 36(6):2565, 2009, Abstract for AAPM 51$^{st}$ Annual Meeting.

Bressan, A., et al., "High Rate Behavior and Discharge Limits in Micro-Pattern Detectors," Nucl. Intr. and Meth. Phys. Research A, 424:321-342, 1999.

Diffenderfer, E., et al., "Determination of Neutron Dose Due to a Therapeutic Proton Beam Incident on a Closed Tungsten MLC Using the Dual Hydrogenous/Non-Hydrogenous Ionization Chamber Method," Med. Phys., 36(6):2733, 2009. Abstract for AAPM 51st Annual Meeting.

Diffenderfer, E., et al., "Development of a System to Measure Neutron Microdosimetry Spectra in a Mixed Proton-Neutron Field," Med. Phys., 36(6):2427, 2009. Abstract for AAPM 51$^{st}$ Annual Meeting.

Dolney, D., et al., "Monte Carlo Simulations to Configure a Treatment Planning System for Modulated Scanning Proton Delivery," Med. Phys., 36(6):2613, 2009. Abstract for AAPM 51$^{st}$ Annual Meeting.

Incerti, S., et al., "Comparison of GEANT4 Very Low Energy Cross Section Models with Experimental Data in Water" Med. Phys., 37(9):4692-4708, 2010.

Kaminski, J., "Micropattern Gas Detectors," In 17$^{th}$ International Workshop on Vertex Detectors, 2008 1-10.

Pedroni, E., et al., "Experimental Characterization and Physical Modeling of the Dose Distribution of Scanned Proton Pencil Beams," Phys. Med. Biol., 50:541-561, 2005.

Rodgers, D., "Fifty Years of Monte Carlo Simulations for Medical Physics," Phys. Med. Biol., 51:R287-R301, 2006.

Zou, J., et al., "Design of a PET Scanner for in Situ Dose Verification in Proton Therapy," Med. Phys., 36(6):2764, 2009. Abstract for AAPM 51$^{st}$ Annual Meeting.

Hollebeek, R., et al., "A New Technology for Fast Two-Dimensional Detection of Proton Therapy Beams," Physics Research International, vol. 2012, (published Dec. 28, 2012), 11 pages.

* cited by examiner

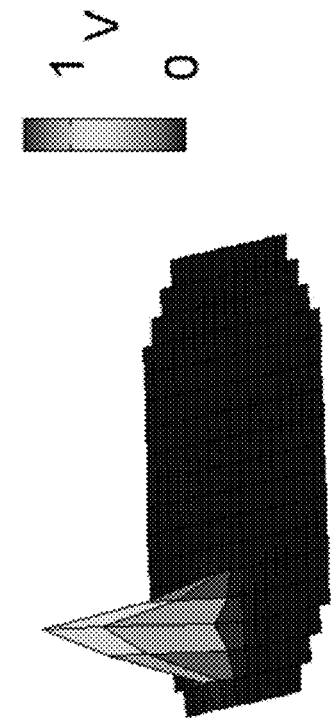
FIG. 5A 504.0 ms
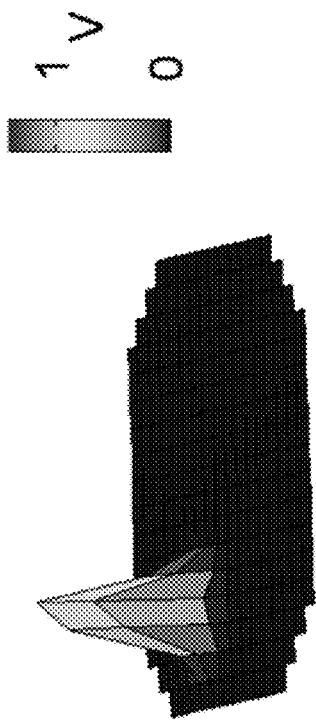
FIG. 5B 512.0 ms
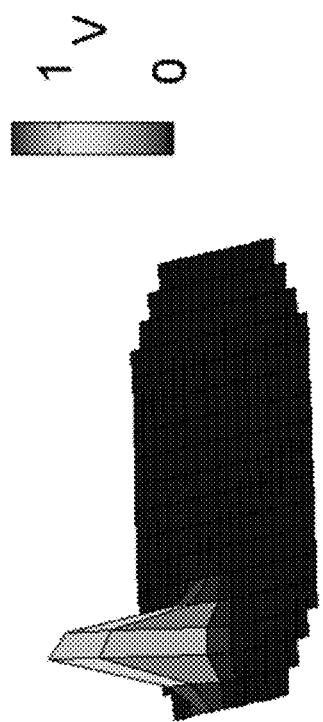
FIG. 5C 521.6 ms
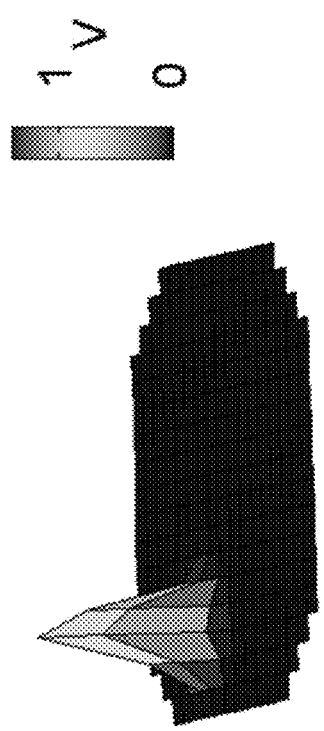
FIG. 5D 528.0 ms

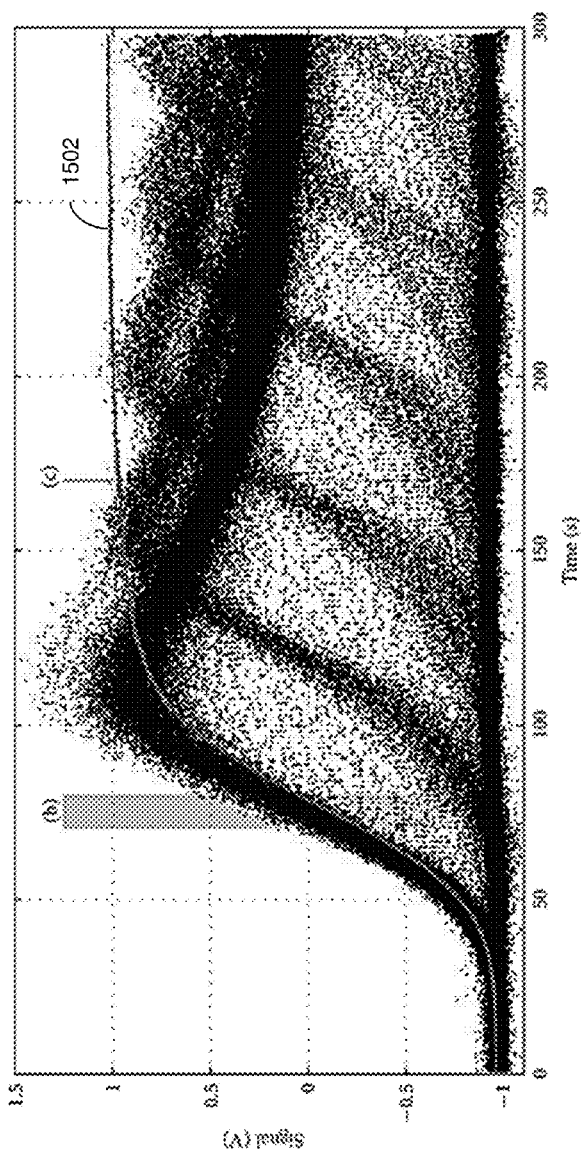
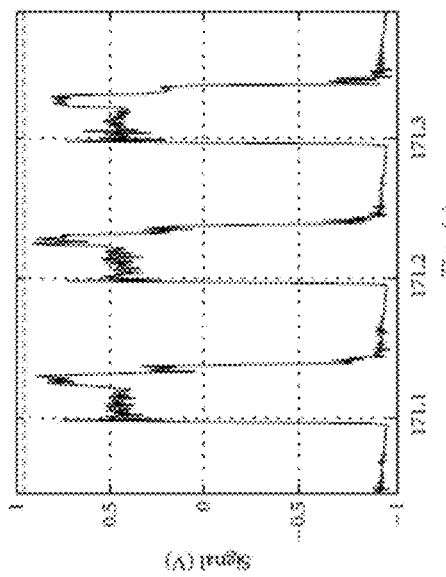
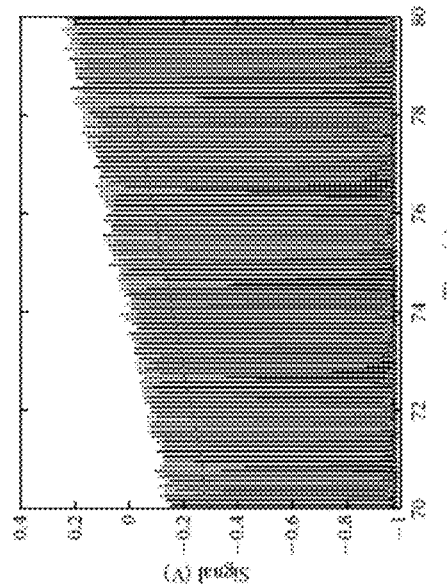
FIG. 15A
FIG. 15B
FIG. 15C

PROTON DOSE IMAGING METHOD AND APPARATUS

CROSS REFERENCE TO RELATED APPLICATION

This application claims priority to U.S. Provisional application Ser. No. 61/862,683 entitled PROTON DOSE IMAGING METHOD AND APPARATUS, filed on Aug. 6, 2013, which is incorporated fully herein by reference.

GOVERNMENT RIGHTS

This invention was made with government support under Contract No. DAMD17-W81XWH-04-2-0022 awarded by the United States Army Medical Research and Material Command. The government has certain rights in the invention.

FIELD OF THE INVENTION

The present invention relates to particle therapy. More particularly, the present invention relates to proton dose imaging methods and proton therapy apparatus using a Micromesh Gaseous Structure (Micromegas) detector.

BACKGROUND OF THE INVENTION

Particle therapy is becoming widely adopted for cancer treatment. Particle therapy (also referred to herein as hadron therapy) is a form of external beam radiotherapy using beams of energetic protons, neutrons or positive ions. Other types of radiation therapy (such as those which use electrons and gamma rays) can control and manage many cancers, but may damage healthy tissue during the therapy process. Particle therapy, in contrast, can be precisely targeted onto the cancerous tumor. The particles may produce a maximum dosage within an extremely small area at a controlled depth in the tissue. The particles, thus, may direct a powerful dose of radiation directly to the tumor, while avoiding unwanted radiation exposure and reducing damage to healthy tissue and vital organs. The precision of particle therapy may be useful for treating tumors in inoperable locations (e.g., the brain, or other locations within the head), near other sensitive tissue (e.g., the spine) and where radiation to normal tissues should be avoided (e.g., for pediatric oncology treatments).

One of the challenges in particle therapy treatments is to improve the quality assurance of the radiation process to ensure that only the tumor is radiated during the treatment.

SUMMARY OF THE INVENTION

The present invention relates to a particle therapy system. A particle therapy system includes a particle beam source for generating a particle beam; and at least one particle detector including an ionization chamber having a mesh electrode. The at least one particle detector is configured to receive the particle beam and to generate an ionization current responsive to the received particle beam. The ionization current is used to characterize the particle beam.

The present invention also relates to methods for particle dose imaging. A method includes generating a particle beam; directing the particle beam to be incident on at least one particle detector including an ionization chamber having a mesh electrode; generating an ionization current by the at least one particle detector response to the received particle beam; and generating a particle dose image of the particle beam based on the ionization current.

BRIEF DESCRIPTION OF THE DRAWINGS

The invention may be understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover, in the drawings, common numerical references are used to represent like features/elements. Included in the drawings are the following figures:

FIGS. 5A, 5B, 5C and 5D are example image frames illustrating particle beam position over a period of time determined using an exemplary particle therapy system, according to an embodiment of the present invention;

FIG. 15A is a graph of signal voltage measurement as a function of time for an exemplary particle therapy system, according to an embodiment of the present invention;

FIGS. 15B and 15C are graphs of signal voltage as a function of time for portions of the graph shown in FIG. 15A;

DETAILED DESCRIPTION OF THE INVENTION

Figure 1:
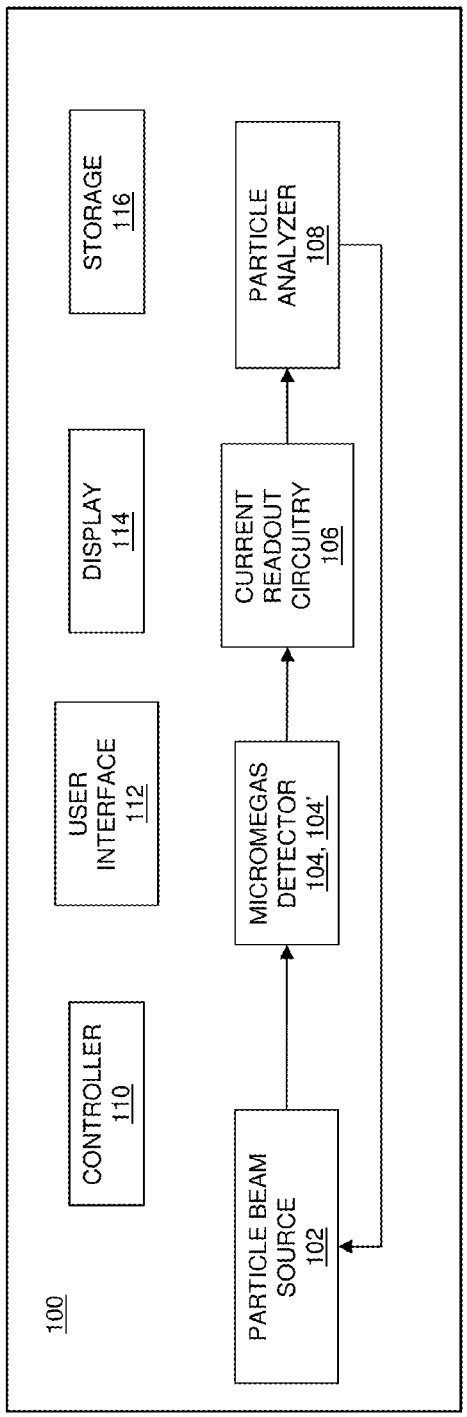
FIG. 1 is a functional block diagram of an example particle therapy system, according to an embodiment of the present invention.

There are currently about 40 hadron therapy facilities in operation worldwide for treating cancer patients with hadrons. Nearly 100,000 patients have completed treatments. The path of a hadron in tissue is essentially straight with relatively low energy loss until very near the end of the range where most energy is deposited in a small region called the Bragg peak, with little exit dose relative to photons. The depth of the Bragg peak in the patient is controlled by the beam energy, and modern delivery systems allow fast and continuous modulation of beam energy during delivery.

Collimation of treatment fields achieves good lateral dose gradients, comparable to X-ray fields, and systems of detectors exist to measure two-dimensional (2D) planes of dose distributions. The steep longitudinal dose gradient that is one motivation behind proton therapy additionally allows for high dose conformity in a third dimension, but currently, there are no detector systems for characterizing three-dimensional (3D) dose distributions.

As an alternative to collimation, narrow proton pencil beams can be scanned magnetically to provide even better dose localization. Although pencil-beam scanning has been used for only a few percent of all hadron treatments to date, a number of the next centers proposed or under construction are planning to offer the scanned-beam technique. Due to the potential for interplay between the motion of the pencil beam and the respiratory motion of the patient, it is necessary to resolve the time structure of the dose delivery to fully realize the capabilities of hadron therapy, particularly for lung tumors.

For direct detection of the high beam current used for hadron therapies, a new generation of dosimetry devices is desired which are capable of high spatial and time resolution accompanied by good linearity and little to no saturation in the Bragg peak. New dosimetry technology tailored to hadron therapy may reduce the uncertainties in beam characteristics (e.g., position, energy/range, stability), partially addressing the range uncertainty problem and potentially allowing for a reduction in treatment margins. This may permit additional disease sites to be treated with particle beams. This may also improve the prospects for dose escalation and hypofractionation strategies, and may generally lower the integral dose to normal tissues across all disease sites.

New dosimetry technology may also accelerate the development and optimization of the next generation of dose delivery technologies, including intensity-modulated scanned pencil beams, especially in conjunction with patient motion management and image-guided radiation therapy (IGRT) systems, by providing good spatial and time resolution for the dose delivery. Dosimetry technology may assist in the development and become components of new and more advanced therapy-supporting technologies including proton radiography, proton-computed tomography, range verification, and range probes, where high spatial and time resolution are important requirements. The dosimetry technology may also facilitate more rapid delivery and commissioning of new particle therapy facilities and allow more comprehensive Quality Assurance (QA) measurements of patient treatment plans to be performed.

For an ideal beam monitoring device used for the characterization of proton therapy beams, it is desirable that the beam position be resolved at the order of about 1 mm and that dose may be measured with an accuracy of about 2% or better. Ionization chambers represent the gold standard for dose accuracy because the gain depends only on ionization in the gas mixture used. For good spatial resolution, multiple chambers may be used. A high amplifier gain required to detect the small signals leads to limited bandwidth and therefore limited time resolution. If using a single chamber, it must be repositioned to obtain beam profiles. This is very time consuming whether done manually or using stepping motors.

Multiple devices can be placed in the beamline to obtain some spatial resolution from a single beam delivery, and one and two dimensional arrays of ionization chambers are available commercially and useful for proton therapy measurements. Semiconductor detectors are also a possible choice for proton therapy dosimetry as they can be made small and thus provide good spatial resolution, and they can be read out fast for good time resolution. However, semiconductor detectors tend to be expensive for large volume arrays, suffer degradation from radiation exposure, and have a response depending on energy, temperature, and dose rate.

Detector systems based on scintillating materials can be manufactured at relatively low cost and can provide good resolution in 2D using planes of scintillating material and in 3D using a volume of scintillator. Thus far, however, scintillating devices used in proton therapy beams suffer from radiation damage and some saturation in the Bragg peak, though it appears that corrections can be made to obtain a reasonable calibration. Chemical dosimeters, including ferrous (Fricke) gels and polymer gels, can be poured into containers of different sizes and shapes and irradiated, followed by readout by methods such as magnetic resonance imaging (MRI) or optical computed tomography (CT), but these, like film, are strictly integrative materials that offer no time resolution.

A typical proton therapy irradiation will deliver 2 Gray (Gy) to a 1 L volume in 1-2 minutes, mostly by direct ionization of tissue molecules, meaning that ion pairs are created in the volume at a rate of a few hundred $\mu A$. A small chamber with an active volume of 1 $mm^3$ would see only a few hundred pA. The dose profile at the edges of the treatment field falls off like an error function, and ideally one would like to resolve the dose in this penumbra at the level of 1% of the maximum dose. Therefore, the goal of a dosimeter for proton therapy is to resolve pA-scale currents. In the case of actively scanned beams, the beam may be swept across the chamber volume on millisecond timescales.

Compared to ionization chambers, proportional counters provide larger signals by operating at a sufficiently high field strength such that primary ions in the gas are accelerated enough to produce additional ionization. Counters operating in the proportional region achieve high enough gain for sensitivity to single ionizing particles. Multiwire proportional chambers and drift chambers can be fabricated into devices that cover large volumes. While many traditional chambers of this type were constructed with small diameter wires, there are now competing technologies for this application, including gas electron multiplier (GEM) detectors where the small structures producing the high electric fields are holes, and Micromesh Gaseous Structure, or so-called Micromegas, where the structures are fine meshes.

The Micromegas is a variation of an ionization chamber where a fine mesh is introduced to create a high-field region where large gas gains, up to factors of $10^6$, can be realized. Advantages of this approach include large dynamic range, high rate capability, good time resolution, and fine segmentation. A manufacturing process to produce Micromegas chambers in bulk at relatively low cost has matured, and refinements to the basic design continue to develop.

Aspects of the present invention relate to a particle therapy system and methods for particle dose imaging. An example particle therapy system includes a particle beam source for generating a particle beam; and at least one Micromesh Gaseous Structure (Micromegas) detector configured to receive the particle beam and to generate an ionization current responsive to the received particle beam. The ionization current may be used to characterize the particle beam. In an example particle therapy system, Micromegas technology is adapted for the particle therapy environment, where the device is operated at low gain and is operated in a current mode (rather than in a pulse mode).

According to an example embodiment, the Micromegas detector includes a multichannel Micromegas detector. In the example below, measurements of spatial and time resolution are described and show that the detector resolves a proton Bragg peak without saturation. The inventors believe that this is the first data obtained with this type of detector in a proton therapy beam.

The Micromegas is a technology previously developed for high count-rate applications in high-energy physics experiments. An example particle therapy system of the present invention uses a Micromegas detector, amplifiers and readout electronics adapted to the requirements of the proton therapy environment.

In an example embodiment, the particle therapy system is operated with ionization gains between 1 and 200 and in low and intermediate dose-rate beams, and the digitized signal is found to be reproducible to 0.8%. Spatial resolution is determined to be 1.1 mm (1σ) with a 1 ms time resolution. A range modulator wheel rotational frequency and the thicknesses of its segments are resolved, and results indicate that this information can be quickly measured owing to the high time resolution of the system. The example particle therapy system resolves a high dose rate within a proton Bragg peak. Systems of the present invention may be useful in future treatment methods involving beams that change rapidly in time and spatial position.

Although the description below describes proton therapy, it is understood that particle therapy systems of the present invention may be adapted for other particle types. For example, the particle therapy system may be used for particles such as neutrons and/or positive ions.

An exemplary system will now be described with reference to the individual figures. FIG. 1 is a functional block diagram illustrating exemplary particle therapy system 100. System 100 includes particle beam source 102, Micromegas detector 104 (or 104'), current readout circuitry 106 and particle analyzer 108. System 100 may also include one or more of controller 110, user interface 112, display 114 and storage 116. Suitable controllers 110, user interfaces 112, displays 114 and storage 116 will be understood by one of skill in the art from the description herein. Particle beam source 102, Micromegas detector 104 (104'), current readout circuitry 106, particle analyzer 108, controller 110, user interface 112, display 114 and storage 116 may be coupled together via a data and control bus (not shown). Although not shown, Micromegas detector 104 (104') may be coupled to a voltage source (described further below with respect to FIG. 2A).

Particle beam source 102 may be configured to generate a particle beam. The particle beam may include any suitable particle such as protons, neutrons, positive ions, electrons and/or photons. Particle beam source 102 may generate the particle beam via any suitable mechanism, such as, without being limited to, proton double-scattered, uniform-scattering and pencil-beam scanning.

Micromegas detector 104 (104') may be configured to receive a particle beam from particle beam source 102 and to generate an ionization current. As described further below, Micromegas detector 104 (104') may simultaneously generate a plurality of ionization currents associated with an area of detector 104 (and/or a volume of detector 104'). Micromegas detector 104 (104') is described further below with respect to FIGS. 2A-2D.

Current readout circuitry 106 may be configured to receive ionization current from Micromegas detector 104

(104') and to generate a digitized signal for each ionization current. Circuitry 106 may also amplify the ionization current prior to digitization. Circuitry 106 is described further below with respect to FIG. 3.

Particle analyzer 108 may be configured to receive a digitized signal from circuitry 106 corresponding to each ionization current. Based on the ionization current, particle analyzer 108 may determine at least one characteristic of the particle beam. For example, plural ionization currents (after digitization) may be formed into a 2D image (from Micromegas detector 104) or a 3D image (from Micromegas detector 104'). The image may be analyzed to detect the beam position, beam arrival time, beam momentum and/or beam dose distribution.

User interface 112 may be used to initiate particle beam measurements. In addition, user interface 112 may be used to select the voltage provided to Micromegas detector 104 (104') for detection of the ionization current. User interface 112 may further be used to select parameters for particle beam source 102, circuitry 106, particle analyzer 108, display 114 and/or for values to be stored in storage 116. User interface 112 may include any suitable interface for initiating measurements, indicating storage, analysis and/or display of quantities. User interface 112 may further include an input device such as a keypad for entering information.

Display 114 may be configured to display one or more ionization currents, images and/or characterization results. It is contemplated that display 114 may include any display capable of presenting information including textual and/or graphical information.

Controller 110 may be configured to control/implement particle beam source 102, Micromegas detector 104 (104'), circuitry 106 and particle analyzer 108 (for example, responsive to user inputs received from user interface 112). Controller 110 may also store values for ionized current and analysis results. Controller 110 may be a conventional digital signal processor, logic circuit or a microprocessor. It will be understood by one of skill in the art from the description herein that one or more of the functions of particle beam source 102 and particle analyzer 108 may be implemented in software and may be performed by controller 110.

Storage 116 may store ionization current from circuitry 106 (and/or from Micromegas detector 104 (104')); particle beam parameters from particle beam source 102 and/or images and/or analysis results from particle analyzer 108. Storage 116 may be a memory, a magnetic disk, a database or essentially any local or remote non-transitory, tangible device capable of storing data.

It will be understood by one of skill in the art from the description herein that Micromegas detector 104 (104') and current readout circuitry 106 may be located remote from particle analyzer 108, such as for remote measurements. Circuitry 106 may be connected to particle analyzer 108 by any suitable wired or wireless connection.

It is contemplated that particle therapy system 100 may be configured to connect to a global information network, e.g., the Internet, (not shown) such that the ionization current and/or analysis results may also be transmitted to a remote location for further processing and/or storage.

Figure 2A:
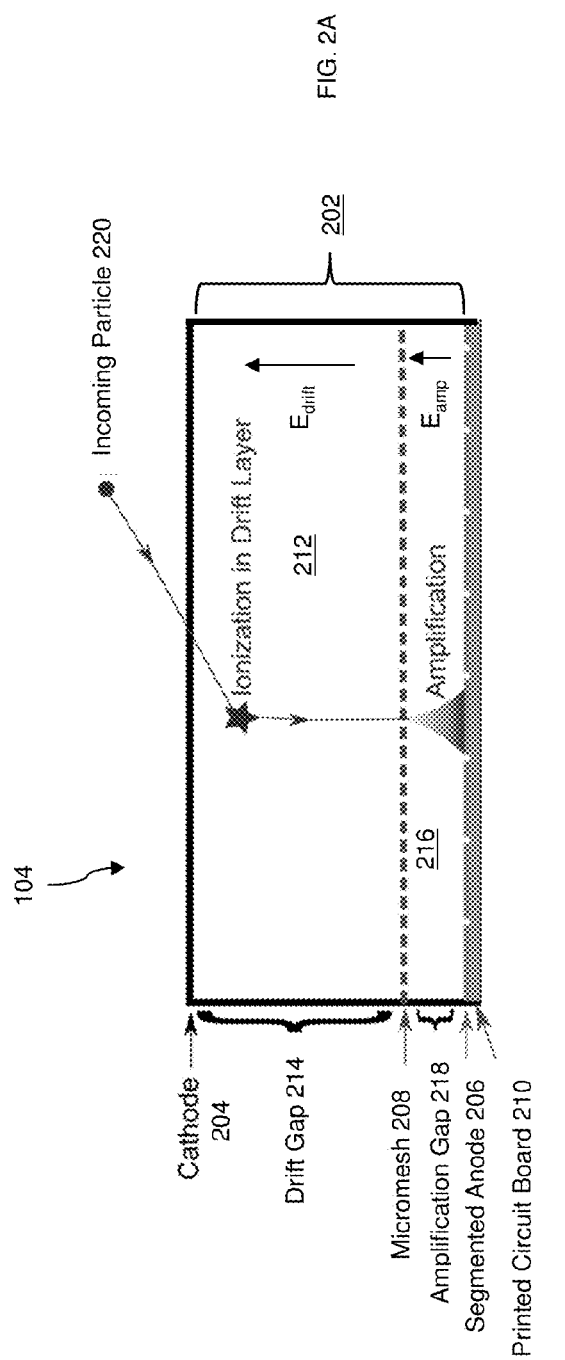
FIG. 2A is a cross-section diagram of an example Micromegas detector of the system shown in FIG. 1, according to an embodiment of the present invention.
Figure 2D:
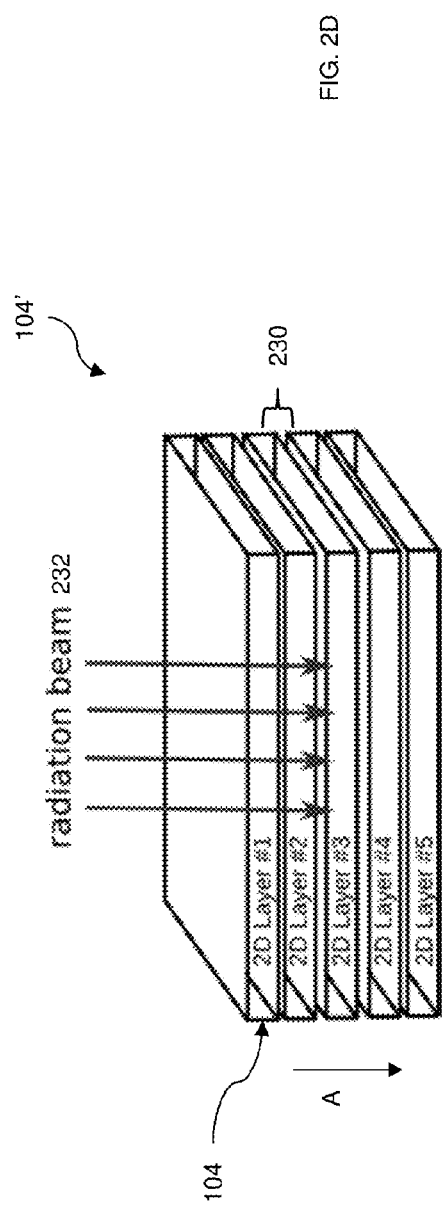
FIG. 2D is a perspective view diagram of an example Micromegas detector of the system shown in FIG. 1, according to another embodiment of the present invention.
Figure 2C:
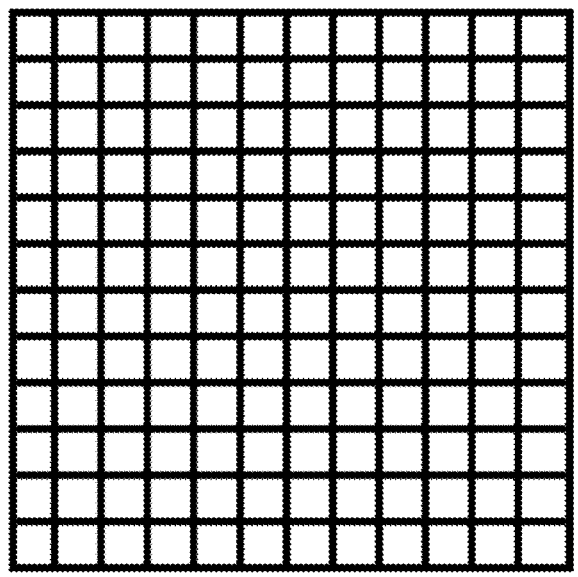
FIGS. 2B and 2C are overhead view diagrams illustrating example anode arrangements of the Micromegas detector shown in FIG. 2A, according to an embodiment of the present invention.
Figure 2B:
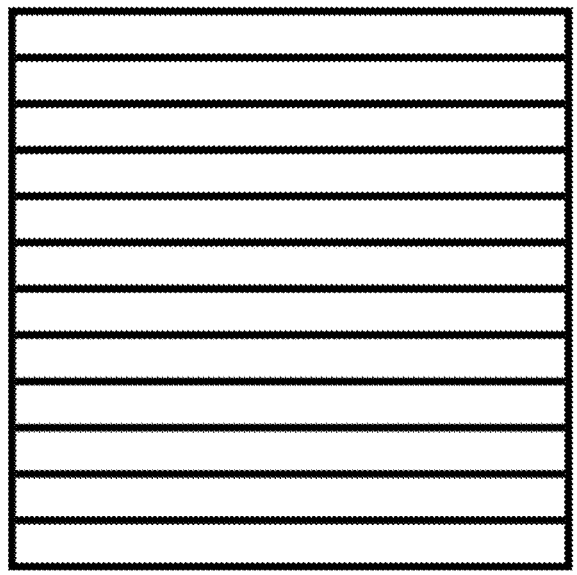

Referring next to FIGS. 2A-2D, exemplary Micromegas detectors 104 and 104' are shown. In particular, FIG. 2A is a cross-section diagram of Micromegas detector 104 capable of producing a 2D particle beam image; FIG. 2B is an overhead view diagram of segmented anode 206 of Micromegas detector 104 in a strip configuration; FIG. 2C is an overhead view diagram of segmented anode 206 in a pixel configuration; and FIG. 2D is a perspective view diagram of Micromegas detector 104' capable of producing a 3D particle beam image.

Referring to FIG. 2A, Micromegas detector 104 includes gas chamber 202, cathode 204, anode 206 and micromesh 208. Cathode 204, anode 206 and micromesh 208 may be planar electrodes which are parallel to each other. Anode 206 may be disposed on printed circuit board 210.

Cathode 204 and micromesh 208 may delimit a drift layer 212. A thickness of drift layer 212 may be designated as drift gap 214. Micromesh 208 and anode 206 may delimit an amplification layer 216. A thickness of amplification layer 216 may be designated as amplification gap 218.

Gas chamber 202 is desirably filled with a low gain mixture of gas. In an exemplary embodiment, the mixture is about 70% argon+30% $CO_2$. Any suitable gas mixture may be used in gas chamber 202 provided that the mixture provides a low gain. As described further below, the amount of gain provided by the gas mixture relates to the amount of amplification of the particles by an avalanche process.

Cathode 204 may be any suitable shape and may be formed of any suitable electrically conductive material. Micromesh 208 may be a thin electrically conductive wire mesh (indicated by the dashed line).

Figure 6:
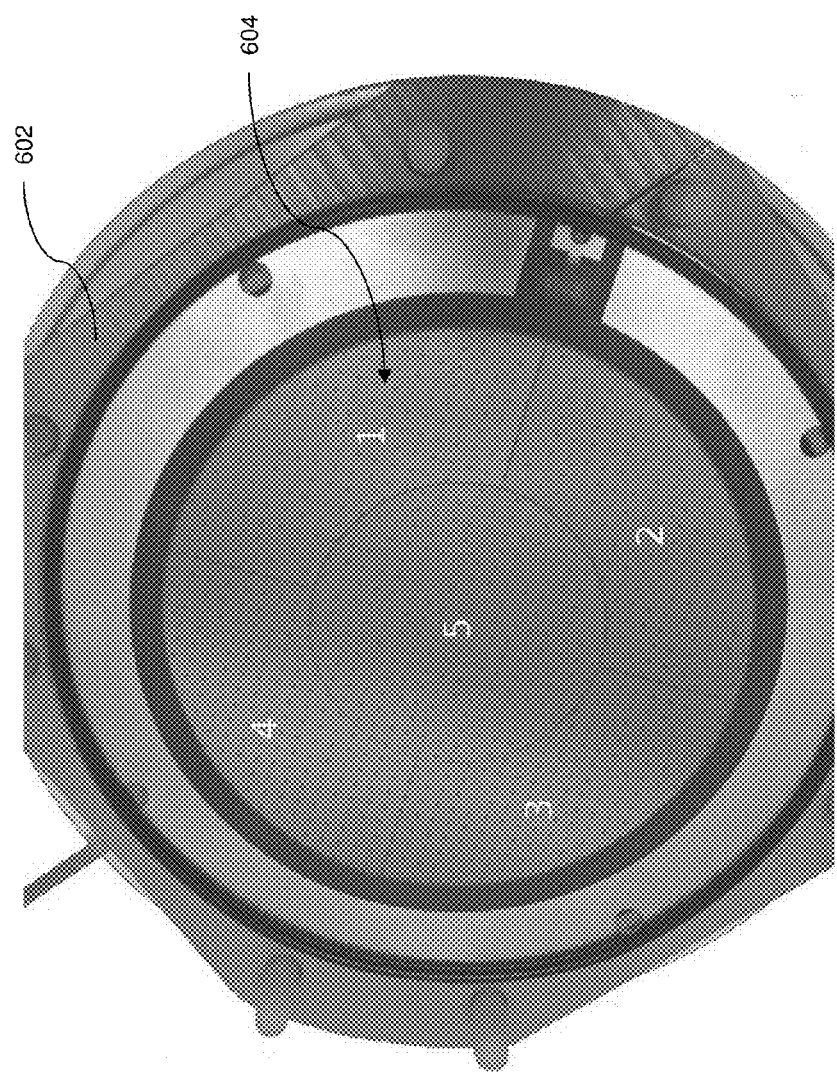
FIG. 6 is a picture of an example anode arrangement of an exemplary Micromegas detector, according to an embodiment of the present invention.

Anode 206 may be formed from a plurality of electrically conductive segments. The segments may be spaced apart from each other and formed on an electrically insulating support (such as printed circuit board 210). FIGS. 2B and 2C illustrate different arrangements of the segments. In FIG. 2B, the segments are arranged as parallel strips. In FIG. 2C, the segments are arranged in a 2D grid of pixels (i.e., a checkerboard pattern). FIG. 6 illustrates a further arrangement of the anode segments.

In general, segments of anode 206 may be formed in any suitable arrangement with any suitable number of segments to detect and to characterize the particle beam. For example, the anode shown in FIG. 2B may detect movement of the particle beam in a horizontal direction (i.e., perpendicular to the direction of the parallel strips. The anode shown in FIG. 2C may detect movement in both vertical and horizontal directions.

The segments of anode 206 are also referred to as output channels, which each output an ionization current. The number of segments of anode 206 (the number of output channels) may control a resolution of the image that is obtained by particle analyzer 108. Accordingly, fewer anode segments may produce a coarser image resolution compared to a greater number of anode segments.

In the example detector 104 shown in FIG. 2A, anode 206 is connected to ground, and the potentials applied to cathode 204 and micromesh 208 are both negative. For example, the potential applied to cathode 204 is about −700 V and the potential applied to micromesh 208 is between about −400 V to about −600 V.

Drift layer 212 and amplification layer 216 are described further below. In general, Table 1 below describes various exemplary design parameters of detector 104 of particle therapy system 100 (FIG. 1) in accordance with aspects of the invention, and compares these parameters to a Micromegas detector used in existing particle physics applications. As can be seen in Table 1, detector 104 has a wider drift gap 214 to collect more primary ionization, has a low gain gas mixture and produces a lower gain compared with Micromegas detectors for particle physics applications.

TABLE 1

Comparison of Particle Physics and Particle Therapy Micromegas Detectors

| | Existing Particle Physics Applications | Particle Therapy System |
|---|---|---|
| Cathode | Copper-plated circuit board | Copper-plated circuit with calibration pulse input |
| Drift Gap | 1-5 mm, 3 mm typical | 1 cm wider gap to collect more primary ionization |
| Drift Field ($E_{drift}$) | High | low |
| Fill Gas | High gain gas | Low gain mixture 70% argon + 30% $CO_2$ typical |
| Micromesh | Fine woven | Fine woven |
| Amplification Gap | 25-150 μm | 100-1000 μm, 300 μm typical |
| Amplification Field ($E_{amp}$) | High | Low |
| Anode Geometry | Varies by application | Segments, strips pads 2-5 mm pitch |
| Spatial Resolution | 70-100 μm | 75 μm |
| Time Resolution | 10 ns | 50 μs |
| Gain | $10^5$ | 1-1000, 100 typical |
| Dynamic Range | | $2^{16}$ (ADCs) ×10 (DAC range) ×40 (pre-amps) ×20 (mesh potential) ×1000 (gas mixture) |
| Calibration | Varies | Absolute using $^{55}$Fe source |

In operation, incoming particle 220 passes through gas chamber 202 and ionizes the gas located in drift layer 212 and may produce several primary electrons. The negative potential of micromesh 208 (relative to anode 206) causes a high electric field region ($E_{amp}$) in amplification gap 218 (between micromesh 208 and anode 206). Under the effect of the electric field in amplification gap 218, the electrons created by ionization move toward micromesh 208. The arrow in drift layer 212 shows the trajectory of one of these electrons. The electrons pass through the openings of micromesh 208 and move towards anode 206. The crossing through micromesh 208 may be facilitated by the ratio between the electric field ($E_{drift}$) created in drift gap 214 and the electric field ($E_{amp}$) in amplification gap 218.

After passing through micromesh 208, the electrons are amplified by the low gain that exists in amplification gap 218, via the avalanche process. The amplified electrons are then directed to anode 206. Ionization current may be collected from segments of anode 206.

Although FIG. 2A describes a single Micromegas detector 104, a plurality of detectors 104 may be arranged, as shown in FIG. 2D, to form Micromegas detector 104'. Detector 104' includes a plurality of Micromegas detectors 104 in a stacked configuration interleaved with solid water layers 230. The Micromegas detector layers 104 may be operated simultaneously.

In FIG. 2D, five Micromegas detectors 104 are shown. It is understood that any suitable number of Micromegas detectors 104 may be used in detector 104'. In detector 104', ionization current may be collected from one or more channels (i.e., segments of anode 206) of each Micromegas detector 104.

In operation, particle beam 232 (also referred to herein as radiation beam 232) may pass through each detector (layer) 104. The particle beam, thus, may be detected by each layer (Micromegas detector 104) (to record a 2D image) as well as along the depth of detector 104' (the depth direction indicated by arrow A). The multiple layers as well as the multiple channels on each layer (as shown in FIGS. 2B and 2C) may be used to generate a 3D image of the particle beam 232 (e.g., by particle analyzer 108 of FIG. 1). For example, each 2D image may be assembled into a 3D image by particle analyzer 108.

Figure 3:
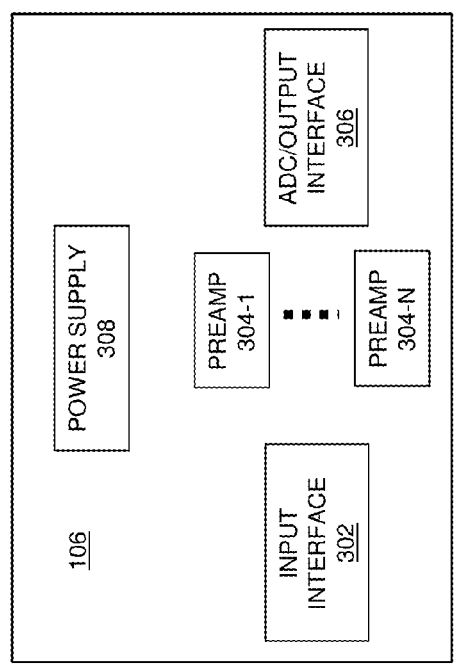
FIG. 3 is a functional block diagram of an example current readout circuitry of the system shown in FIG. 1, according to an embodiment of the present invention.
Figure 8A:
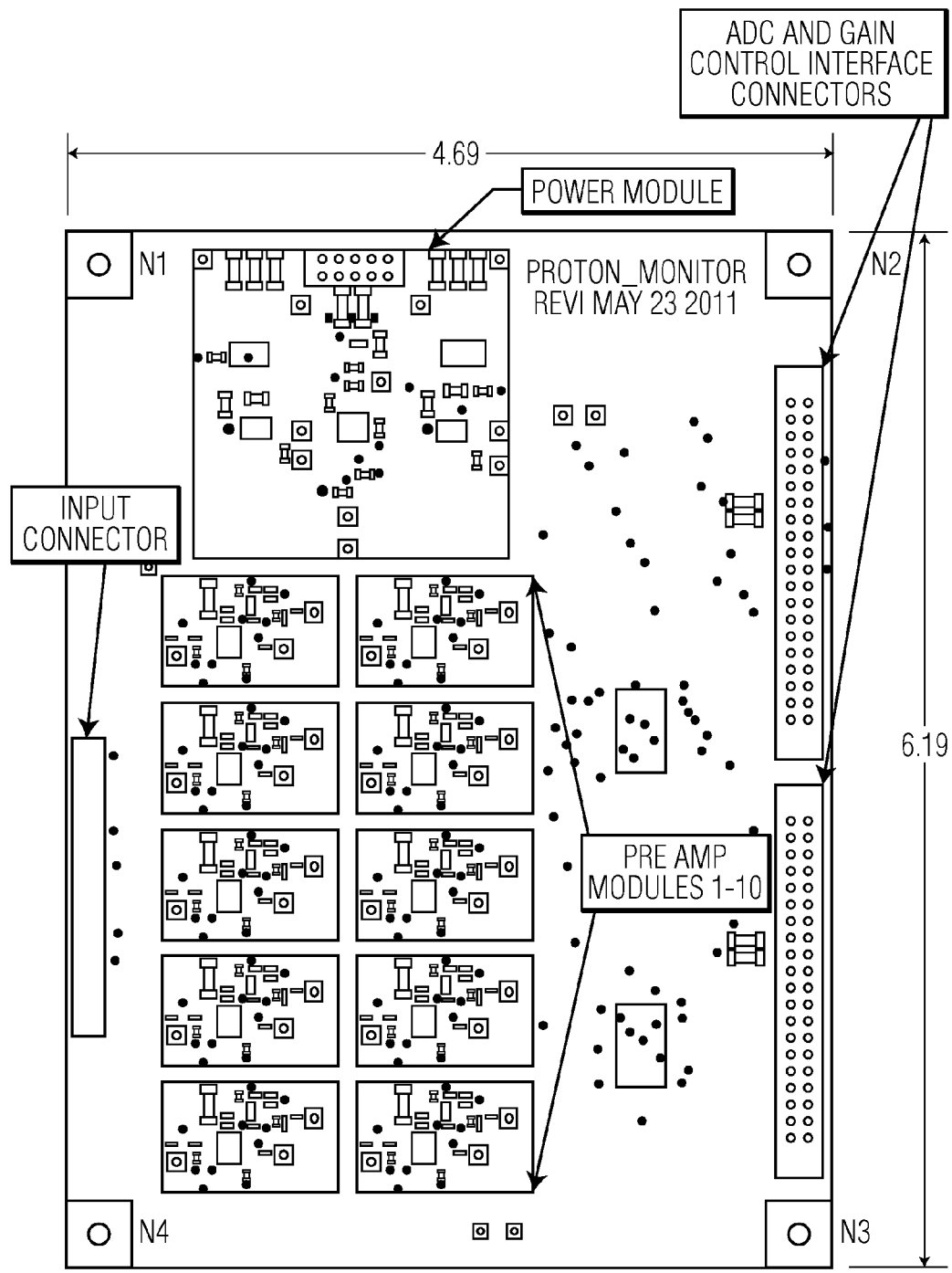
FIG. 8A is a schematic circuit diagram of example current readout circuitry of an exemplary particle therapy system, according to an embodiment of the present invention.

Referring next to FIG. 3, a functional block diagram of current readout circuitry 106 of system 100 (FIG. 1) is shown. Circuitry 106 may include input interface 302, preamplifier (preamp) modules 304-1, . . . , 304-N (where N is greater than or equal to 1), analog to digital converter (ADC)/output interface 306 and power supply 308. A further example of current readout circuitry 106 is shown in FIG. 8A. A plurality of circuitry 106 modules may be used for Micromegas detector 104' (FIG. 2D), with each module corresponding to a detector layer of detector 104'.

In general, input interface 302 is coupled to output channels of Micromegas detector 104 (via segments of anode 206 (FIG. 2A)). Input interface 302 directs the ionization current from each output channel to respective preamplifier modules 304. In one example, each output channel of detector 104 may correspond to one preamplifier module 304 (e.g., a first output channel may correspond to preamplifier module 304-1). According to another example, each output channel may correspond to multiple preamplifier modules (e.g., modules 304-1 and 304-2), where the modules have different gain settings (e.g., high gain and low gain) associated with different particle beam delivery techniques (such as for double-scattered and modulated-scanned delivery techniques).

Each preamplifier module 304 may receive the ionization current from the respective output channel of detector 104, via input interface 302, and may generate an amplified signal, according to a predetermined gain setting. As discussed above, the gain setting may depend upon the particle beam delivery method (as produced by particle beam source 102 (FIG. 1)). Each amplified signal from preamplifiers 304 may be provided to ADC/output interface 306.

ADC/output interface 306 may convert the (analog) amplified signal from each preamplifier 304 to a digitized signal, and may output the digitized signal (in a suitable format) for analysis by particle analyzer 108 (FIG. 1). Interface 306 may further amplify the output signal (via a digitizer gain).

In general, the net gain of particle therapy system 100 (FIG. 1) may be adjusted based on a digitizer gain in interface 306, the gain setting(s) of preamplifier modules 304 and the gas gain of the micromesh voltage range of detector 104 (FIG. 2A).

Power supply 308 is configured to power preamplifier modules 304, as well as ADC/output interface 306.

Figure 8B:
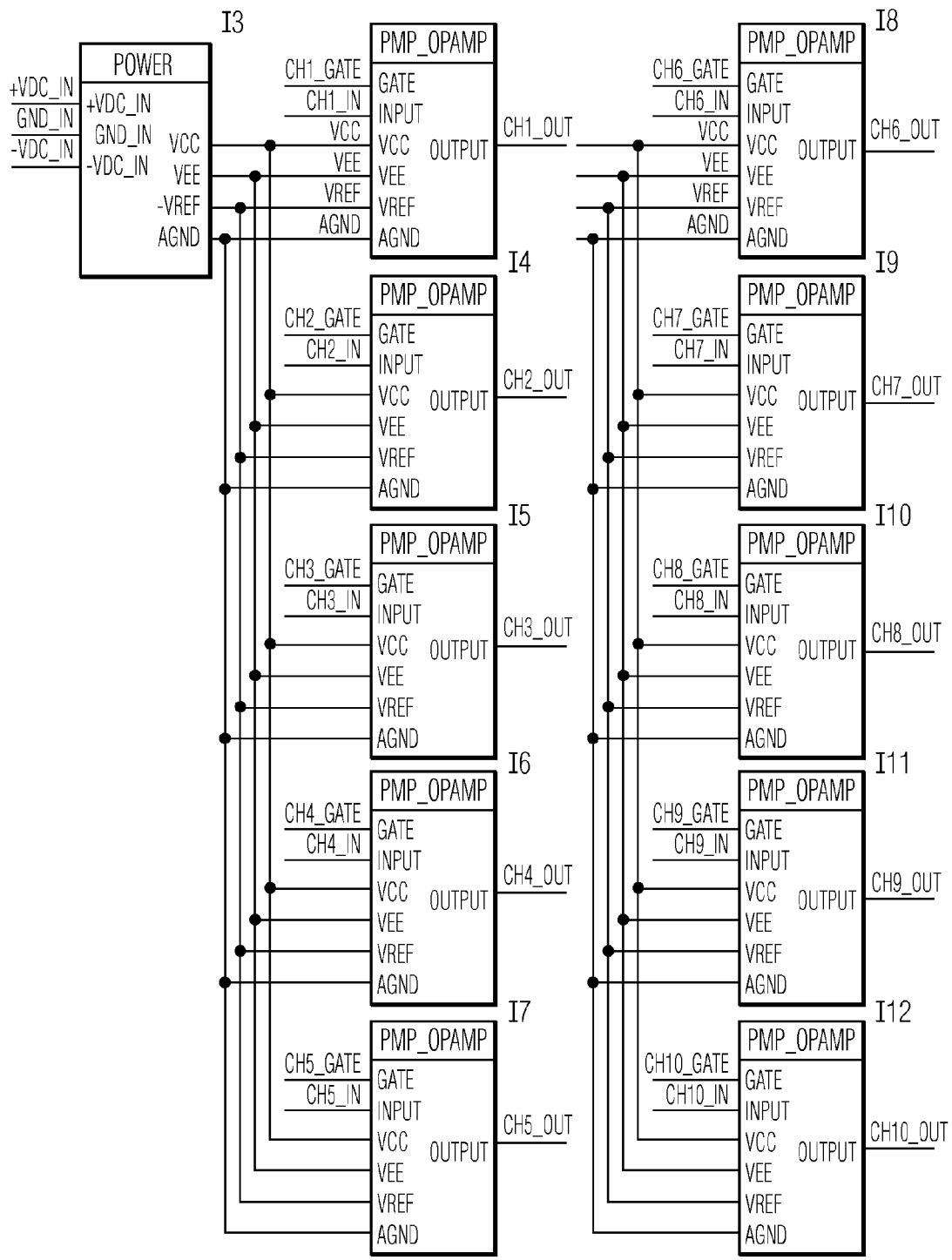
FIGS. 8B, 8C, 8D and 8E are schematic circuit diagrams of portions of the current readout circuitry shown in FIG. 8A, according to an embodiment of the present invention.
Figure 8C:
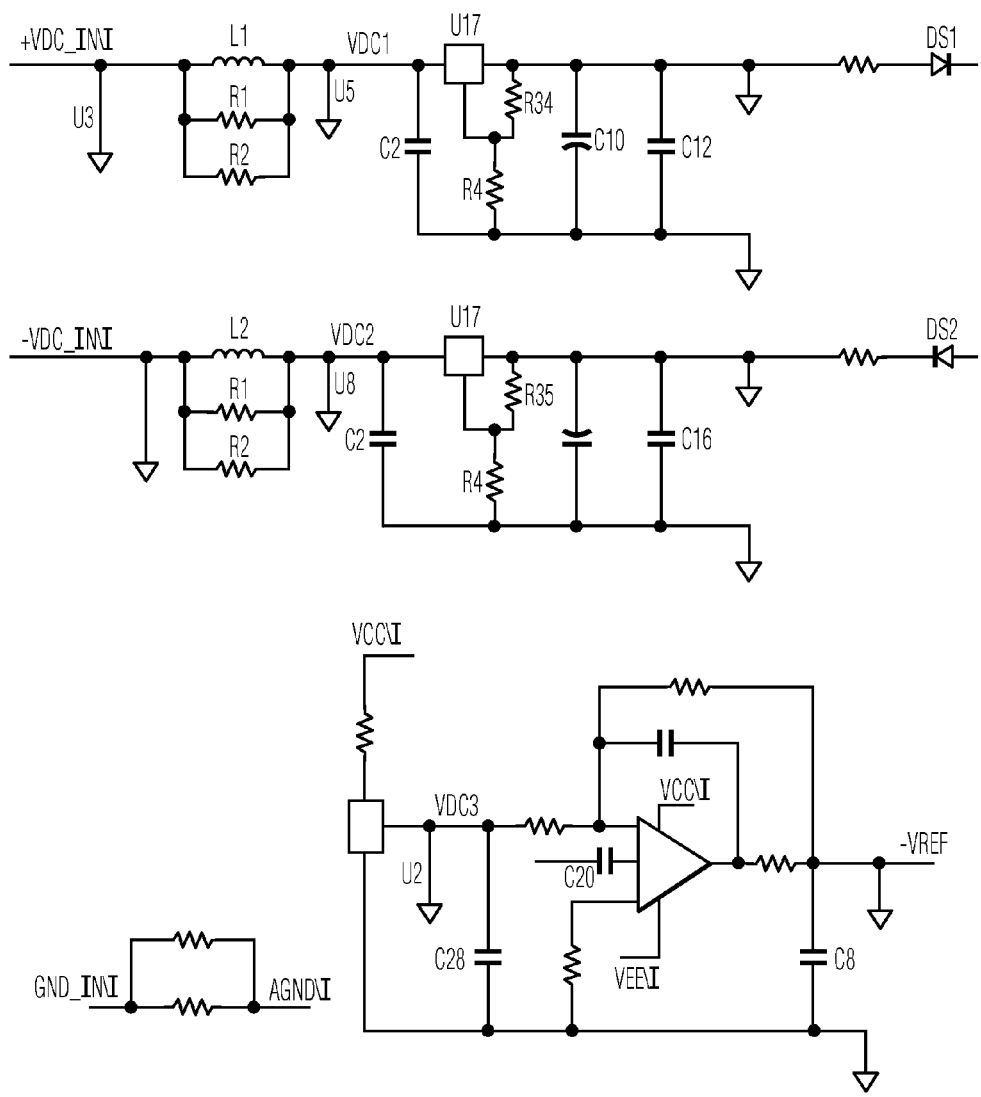
Figure 8D:
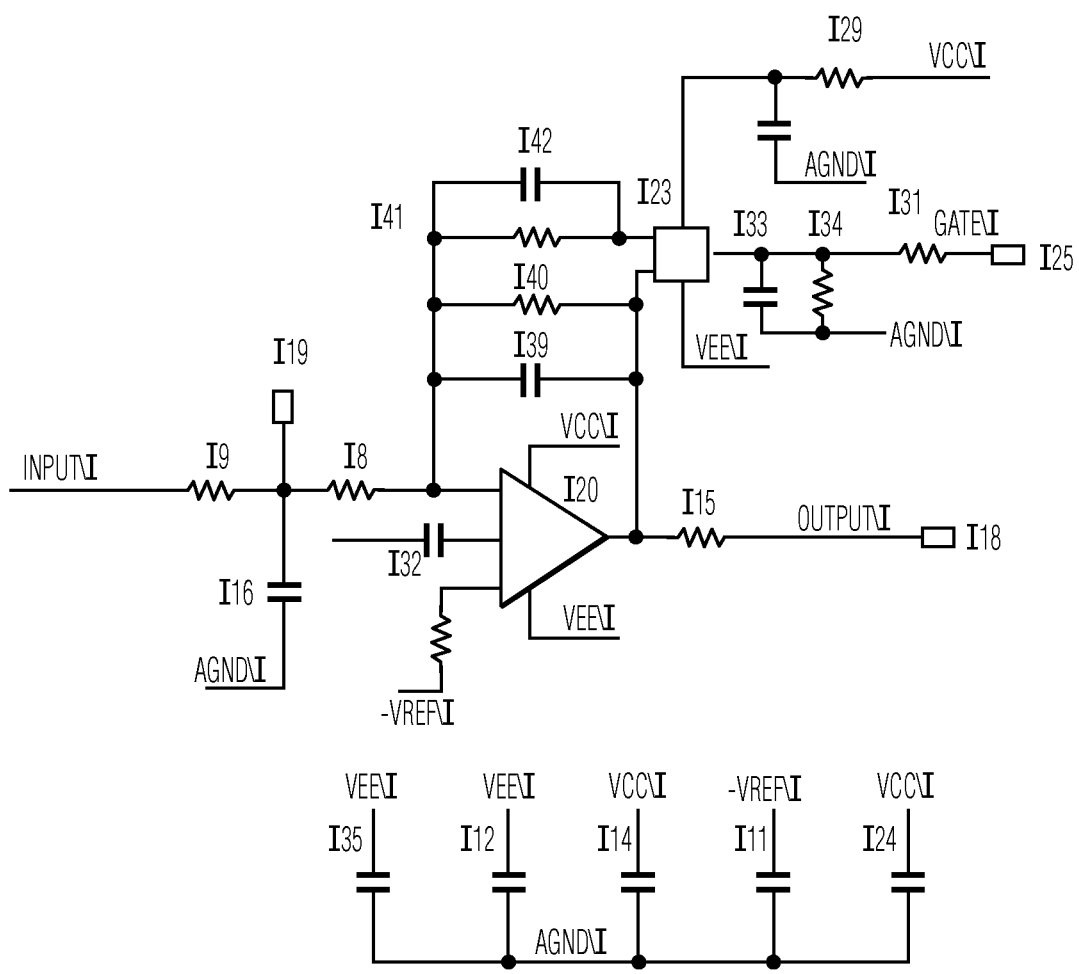
Figure 8E:
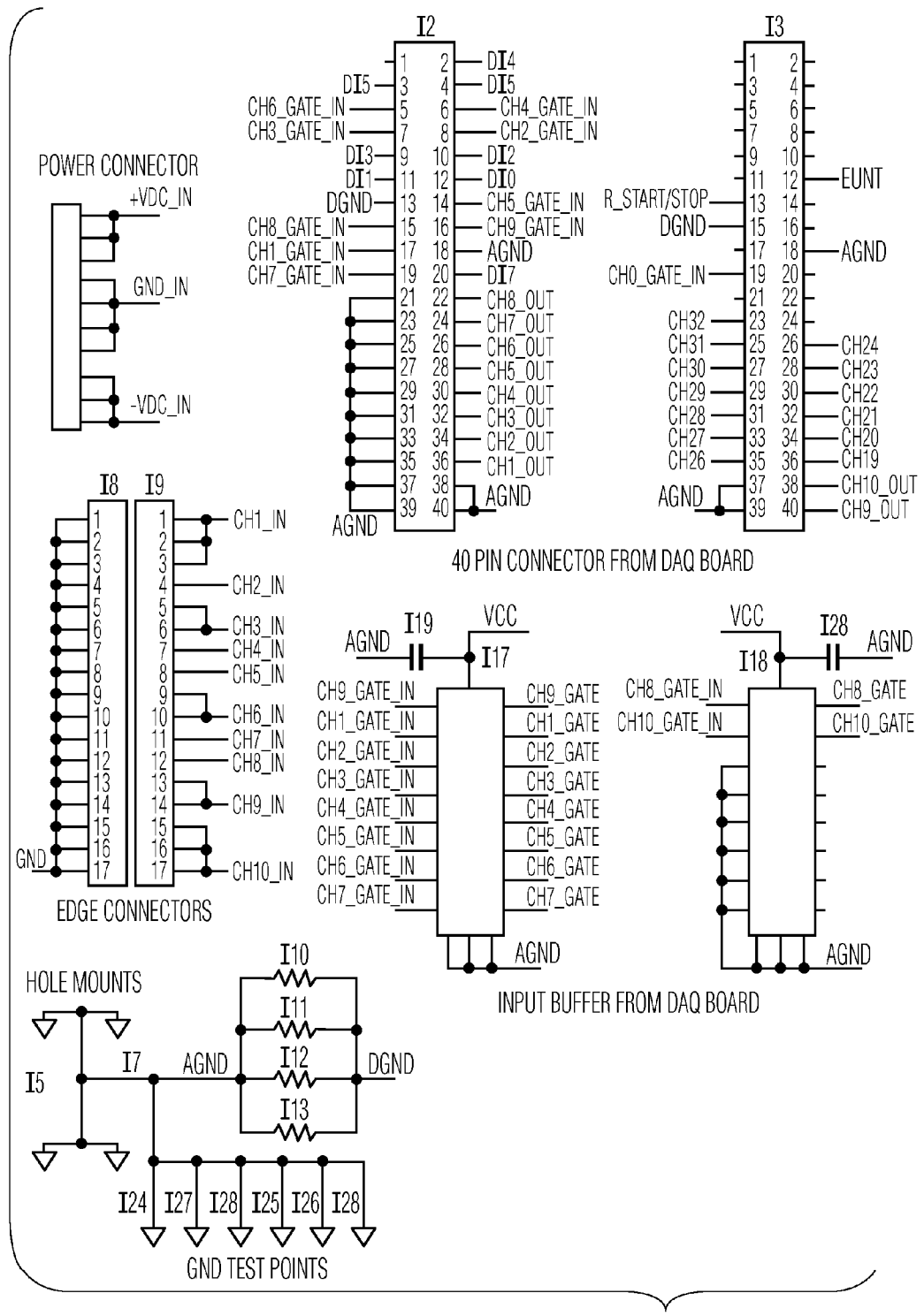

An example current readout circuitry 106 is shown in FIGS. 8A-8E, according to an embodiment of the present invention. In particular, FIG. 8A is a schematic circuit diagram of current readout circuitry for 10 channels configured for low gain and high gain modes; FIG. 8B is a schematic circuit diagram of a preamplifier hierarchy of the current readout circuitry shown in FIG. 8A; FIG. 8C is a schematic circuit diagram of a power module of the current readout circuitry shown in FIG. 8A; FIG. 8D is a schematic circuit diagram of a preamplifier module of the current readout circuitry shown in FIG. 8A; and FIG. 8E is a schematic circuit diagram of interface connectors of the current readout circuitry shown in FIG. 8A.

The current readout circuitry shown in FIGS. 8A-8E is configured for a high gain mode (between about 16 mV/nA to about 20 mV/nA) and a low gain mode (between about 480 mV/μA to about 500 mV//μA). In the high gain mode: a 14 bit ADC is 16384 counts; a DC voltage range is between about 5 V and about 15 V; a least count (as simulated in Simulation Program with Integrated Circuit Emphasis (SPICE)) is 10/16384=0.610 mV/cnt; and a resolution is 36.8 pA/cnt. In the low gain mode: a 14 bit ADC is 16384 counts; the DC voltage range is between about 5 V and about 15 V; a least count (as simulated in SPICE) is 10/16384=0.610 mV/cnt; and the resolution is 1.25 nA/cnt.

Figure 8F:
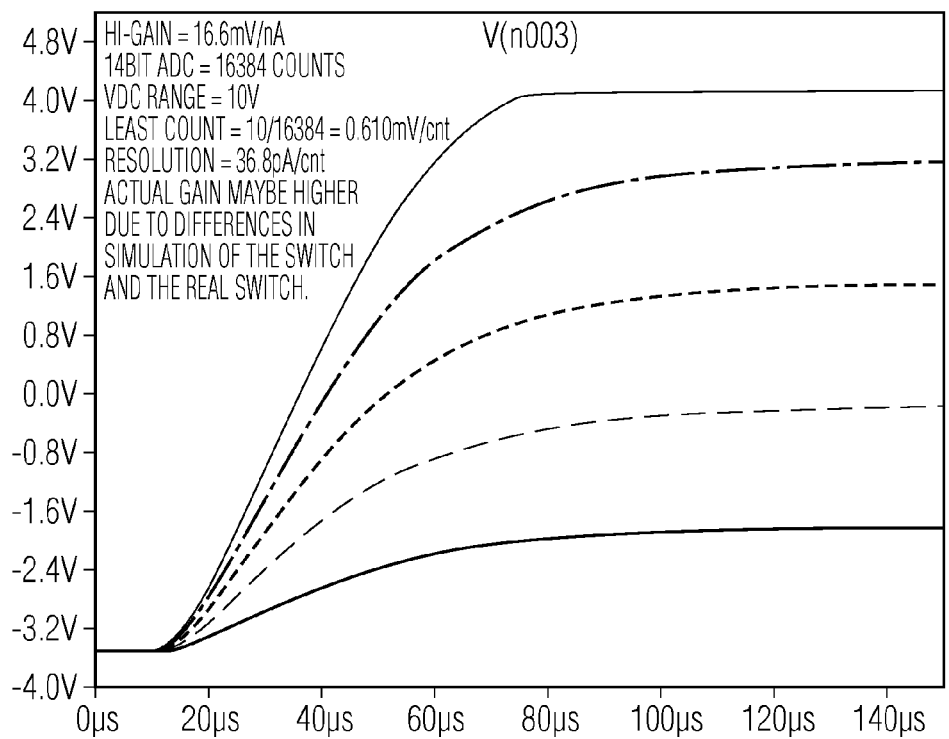
FIGS. 8F, 8G and 8H are graphs of voltage as a function of time for various gain settings and ramp input current for the current readout circuitry shown in FIG. 8A, according to an embodiment of the present invention.
Figure 8G:
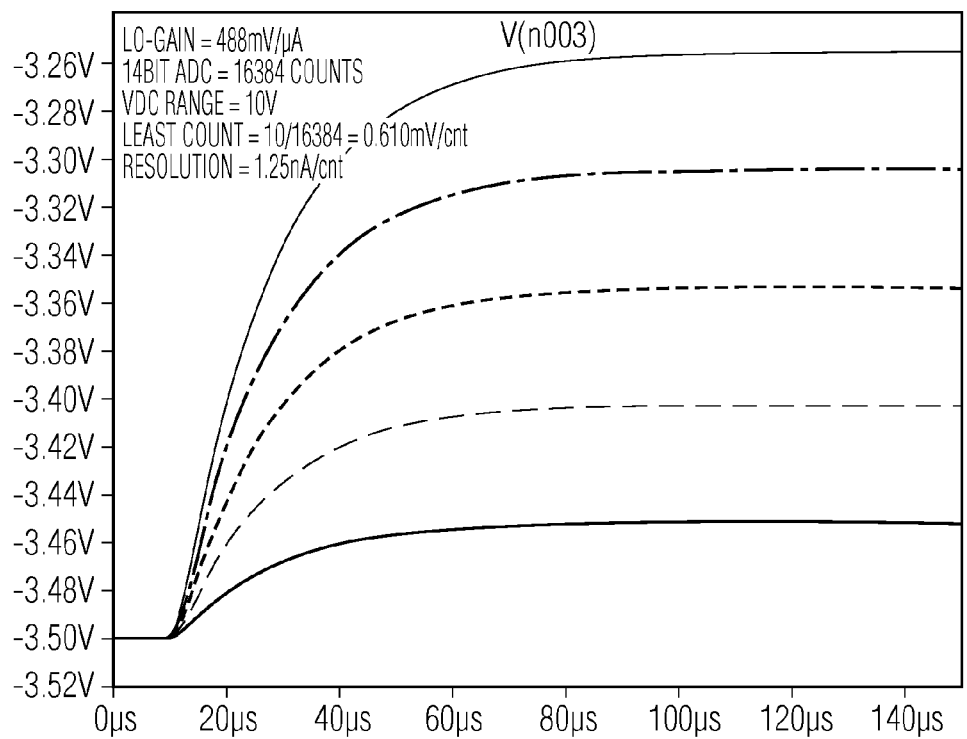
Figure 8H:
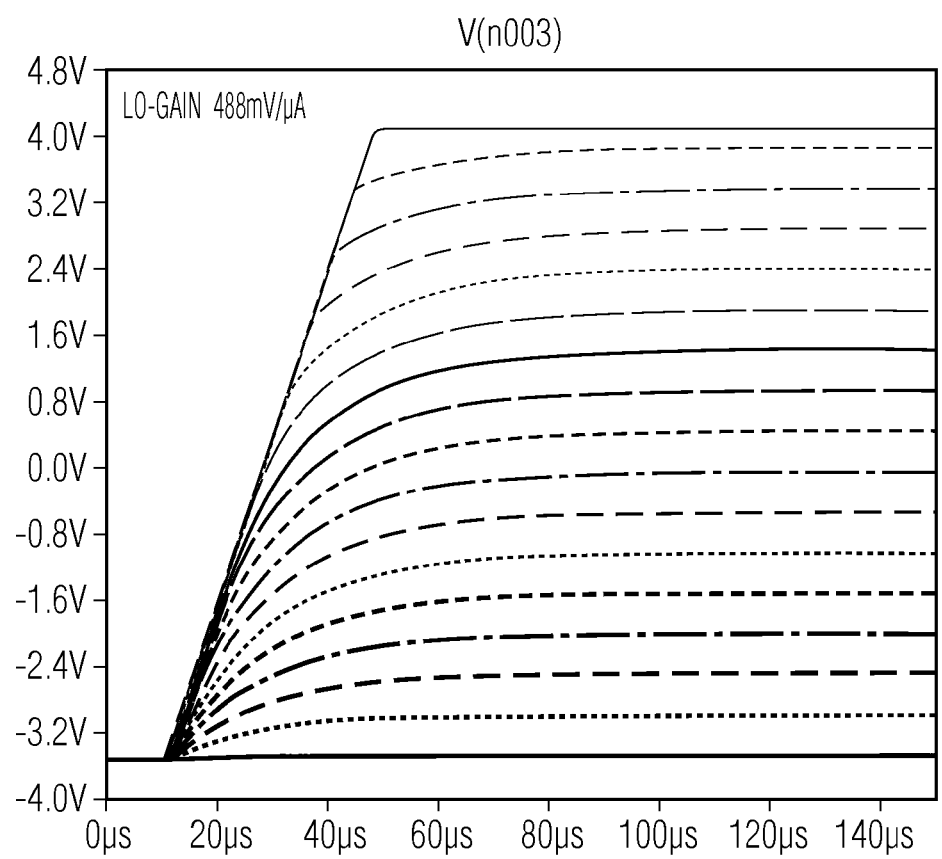

FIGS. 8F-8H are graphs of voltage as a function of time for various gain settings and ramp input current for the current readout circuitry shown in FIG. 8A. FIGS. 8F-8G illustrate the output of the current readout circuitry for ramp input current of 100 nA, 500 nA by 100 nA, for the high gain mode and the low gain mode, respectively. FIG. 8H illustrates the output of the current readout circuitry (for the low gain mode) for ramp input current of 100 nA, 16 μA by 1 μA.

Figure 4A:
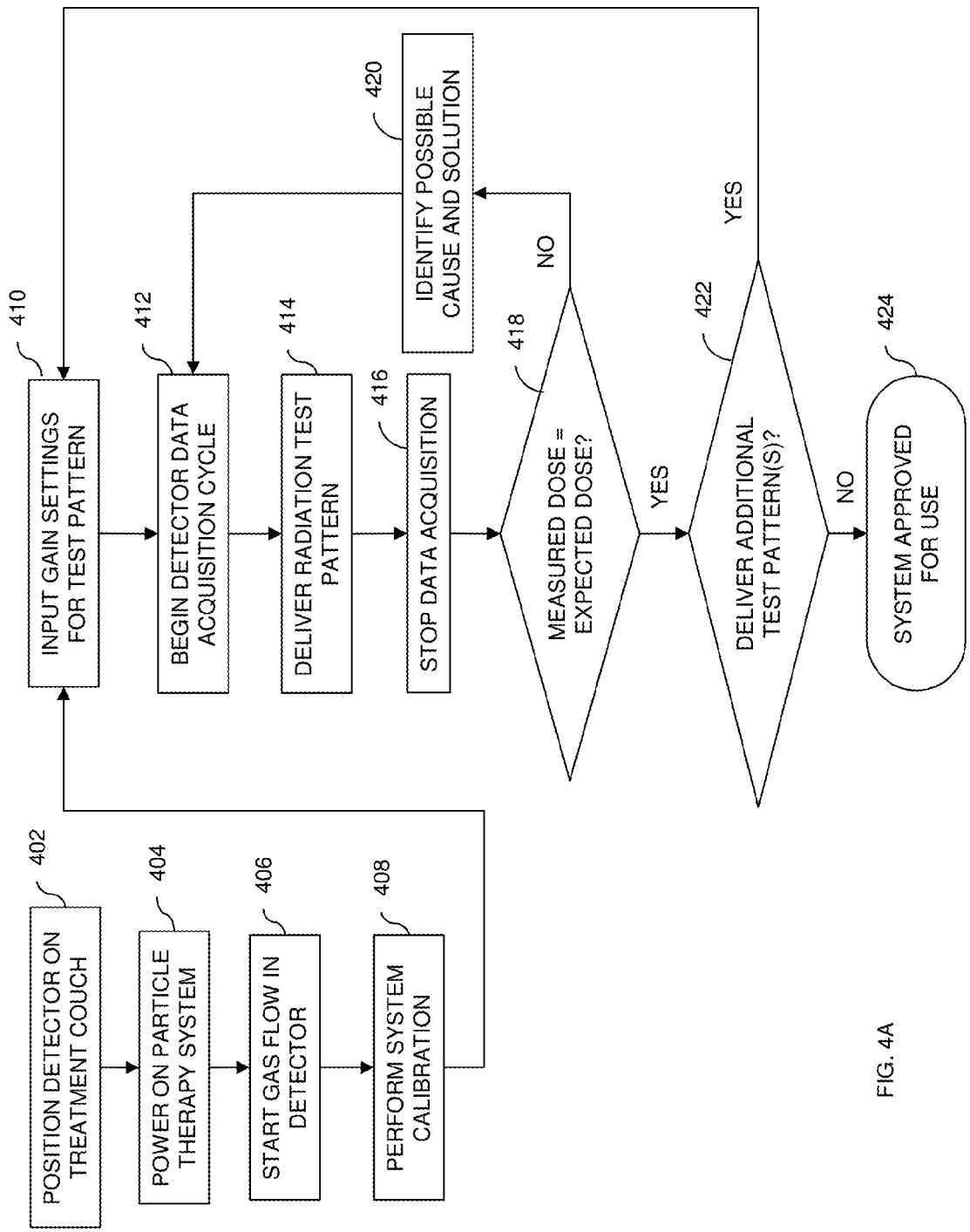
FIG. 4A is a flowchart of an exemplary method for particle dose imaging for machine quality assurance testing, according to an embodiment of the present invention.
Figures 4B, 4C:
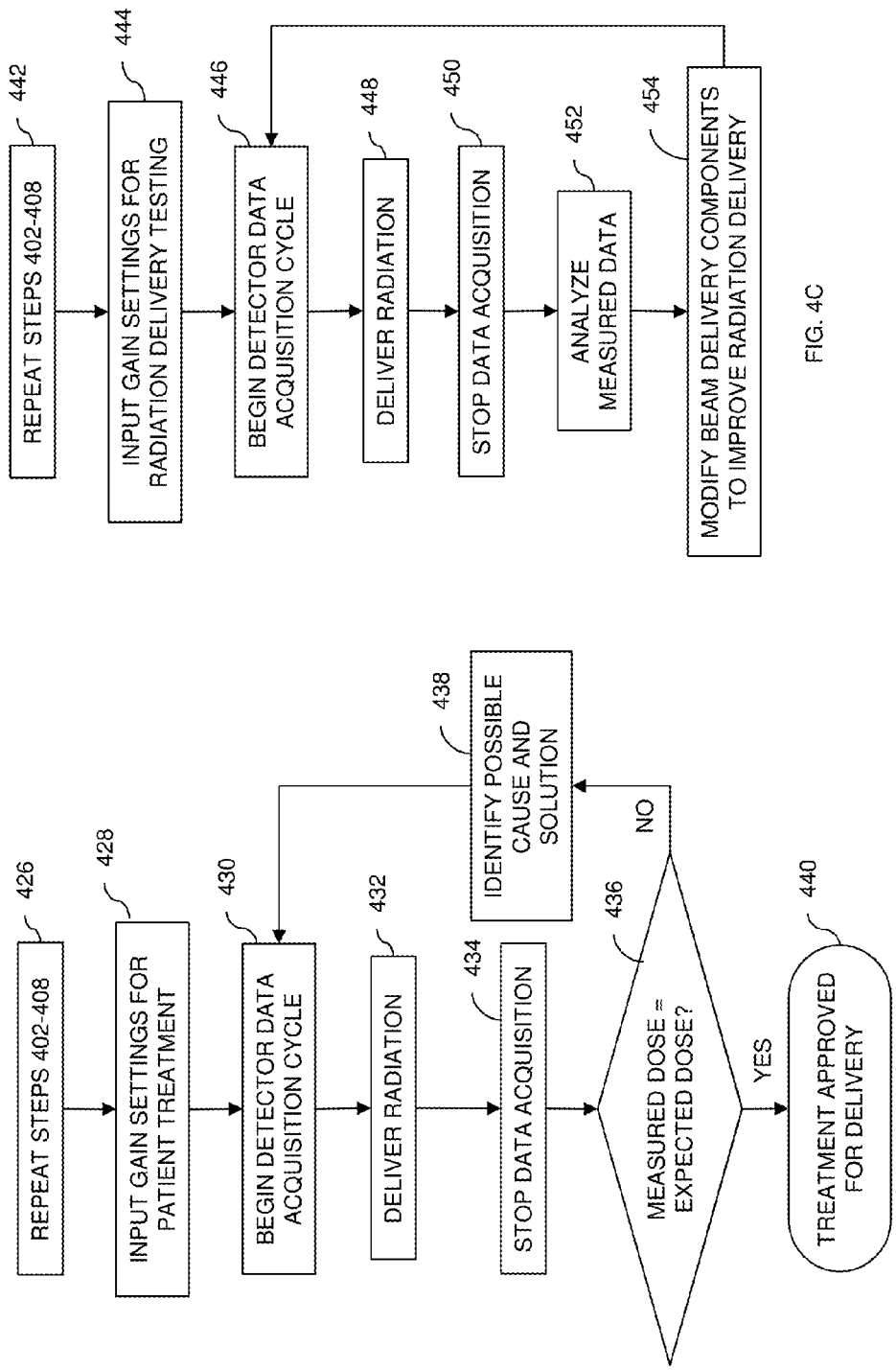
FIG. 4B is a flowchart of an exemplary method for particle dose imaging for patient treatment machine verification, according to an embodiment of the present invention.
FIG. 4C is a flowchart of an exemplary method for particle dose imaging for radiation delivery research and development, according to an embodiment of the present invention.

Referring next to FIGS. 4A-4D, flowcharts are shown which illustrate exemplary methods for particle dose imaging (such as using particle therapy system 100 of FIG. 1), which may be useful in several clinical applications. For example, FIG. 4A describes the use of particle therapy system 100 for machine quality assurance tests; FIG. 4B describes the use of particle therapy system 100 for patient treatment machine verification; FIG. 4C describes the use of particle therapy system 100 for radiation delivery research and development; and FIG. 4D describes the use of particle therapy system 100 for active beam monitoring with feedback to delivery.

Figure 4D:
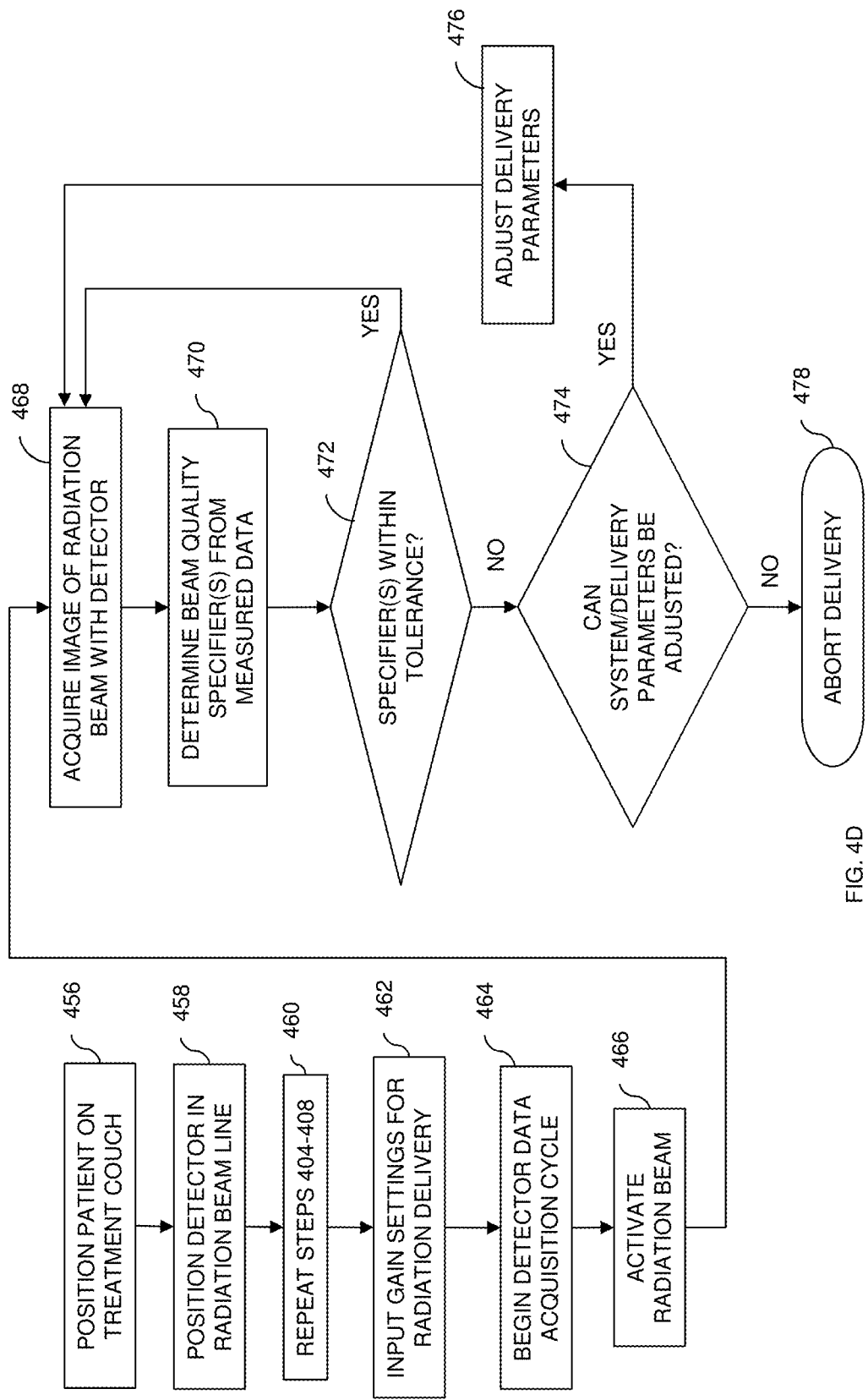
FIG. 4D is a flowchart of an exemplary method for particle dose imaging for active beam monitoring with feedback to delivery, according to an embodiment of the present invention.

Micromegas detector 104 (104') may be positioned anywhere along a radiation line of sight of the particle beam (between particle beam source 102 and the patient). For example, the detector 104 (104') may be positioned on a treatment couch (where a patient would normally be positioned) for machine quality assurance tests (FIG. 4A). The detector 104 (104') may be positioned in a treatment module itself so that feedback from the detector 104 (104') may be used to modify the particle beam (FIG. 4D).

Referring to FIG. 4A, a flowchart is shown of an exemplary method for particle dose imaging for machine quality assurance testing. At step 402, detector 104 (104') is positioned on a treatment couch. At step 404, components of particle therapy system 100 are powered on. For example, detector 104 (104') is powered on via electrical connection to cathode 204 and anode 206 (FIG. 2A). Current readout circuitry 106 may be powered on via power supply 308 (FIG. 3). Additional components of particle therapy system 100 may also be powered on, such as particle analyzer 108, controller 110, user interface 112, display 114 and/or storage 116. At step 406, gas flow into gas chamber 202 of detector 104 (104') is started.

At step 408, calibration of system 100 is performed. Detector 104 (104') may include a calibration source embedded in drift layer 212 (FIG. 2A). Current pulses from the test source, or some other calibration signal, are captured by current readout circuitry 106. In some examples, the calibration signal is applied to a shaping amplifier via current readout circuitry 106. A shaping amplifier may be used for pulse shaping, to filter noise and/or to amplify the output signal of each preamplifier 304 (FIG. 3). The shaping amplifier may be used to improve the pulses for the calibration, by reducing noise and improving a pulse rise time. The collected calibration current pulses are dependent upon the mesh potential, as well as the ambient temperature and pressure. In general, a calibration current pulse height spectrum can be used to correct detector 104 (104') for variations in gain due to changes in gas, voltage, temperature and/or pressure. The calibration may be determined by controller 110 and/or particle analyzer 108, and stored in storage 116. In another example, system 100 may be cross-calibrated relative to a reference chamber. A radiation beam selected to deliver a standard (predetermined) dose is provided to chamber 202 (FIG. 2A) of system 100 (to be calibrated) and also to a reference chamber (not shown). A calibration factor for chamber 202 is derived/adjusted such that the measured dose agrees with that from the reference chamber. In another example, system 100 may be calibrated at an Accredited Dosimetry Calibration Laboratory (ADCL) using a reference beam, such as a $^{60}$Co beam.

At step 410, predetermined gain settings for a radiation test pattern are provided to system 100. The radiation test pattern and the predetermined gain settings may be selected for suitable machine quality assurance tests of system 100. For example, the gain settings may be provided to system 100 by a user via user interface 112 (FIG. 1). In other examples, the predetermined gain settings may be stored in storage 116.

At step 412, a data acquisition cycle is initiated, for example, by controller 110 (FIG. 1). At step 414, a radiation test pattern is delivered to detector 104 (104'), for example, via particle beam source 102. In some examples, operation of particle beam source 102 may be controlled via controller 110. During delivery of the radiation test pattern (step 414), current readout circuitry 106 may capture detector 104 (104') output, and provide a digitized output to particle analyzer 108. The digitized output may also be stored in storage 116. At step 416, the data acquisition cycle ends and the data acquisition is terminated, for example, by controller 110.

At step 418, the measured dose is compared to an expected dose for the quality assurance test. For example, the measured dose may be determined by particle analyzer 108 (FIG. 1) and compared with an expected dose stored in storage 116, via controller 110.

If it is determined, at step 418, that the measured dose is not equal to the expected dose, step 418 proceeds to step 420. At step 420, possible causes for the measured dose not matching the expected dose are determined, and solutions for achieving the expected dose are identified. The measured dose may not equal the expected dose, for example, due to mechanical issues, hardware issues and/or software issues. Examples of mechanical issues may include a device being physically damaged, deformed and/or warped, and/or the radiation beam 232 (FIG. 2D) being blocked by an object in the beam path. The damage and/or obstacle may be located and corrected. Examples of hardware issues may include one or more components of system 100 drifting outside of a predetermined tolerance range, a component reaching an end-of-life cycle (for example, a beam filament may have a weekly replacement schedule) or a failure of one or more components (e.g., failure of a system power supply, electronics, etc.). Failing components may be identified and re-calibrated (if possible) or replaced with new ones (if re-calibration is not possible). Examples of software issues may include unexpected (i.e., sub-optimal) performance of any control and/or monitoring sub-system processing. The non-optimal performance may be identified and corrected. Software and hardware sub-systems may not agree with respect to communication protocols or with respect to specifications of tolerances that indicate error conditions. Software bugs may be identified and corrected. System hardware specifications should be complete and not permit misinterpretation. System 100 may be adjusted according to the solution(s) identified in step 420, and processing proceeds to step 412. In some examples, if no solution is identified at step 420, one or more components of system 100 may be considered to be defective and may not be approved for use.

If it is determined, at step 418, that the measured dose is equal to the expected dose, processing proceeds to step 422. At step 422, it is determined whether there are additional test patterns to be delivered, for example, by controller 110 (FIG. 1).

If it is determined, at step 422, that additional test patterns are to be delivered, processing proceeds to step 410. Steps 410-418 are then repeated for the additional test pattern.

In some examples, a quality assurance test may be associated with one test pattern. In other examples, a quality assurance test may be associated with more than one test pattern. For example, a number of system tests may be performed on a routine basis for comprehensive validation of clinical delivery systems. In general tests may include, without being limited to, delivery patterns for dosimetry (i.e., machine output) validation, beam positioning validation, beam momentum validation, and/or beam dose distribution validation. The indication of the number and specific test patterns to deliver for a particular quality assurance test may be stored in storage 116. Controller 110 may determine that the current test is associated with more than one test pattern, and proceed to step 410 for the specified test pattern. In some examples, system 100 may receive an indication from a user via user interface 112 relating to additional test patterns for testing.

If it is determined, at step 422, that no additional test patterns are to be delivered, step 422 proceeds to step 424. At step 424, it is determined, for example, by controller 110, that system 100 is approved for use.

FIG. 4B is a flowchart of an exemplary method for particle dose imaging for patient treatment machine verification. At step 426, steps 402-408 (FIG. 4A) are repeated. At step 428, predetermined gain settings for a predetermined patient treatment are provided to system 100. For example, the gain settings may be provided to system 100 by a user via user interface 112 (FIG. 1). In some examples, the predetermined gain settings may be stored in storage 116.

At step 430, a data acquisition cycle is initiated, for example, by controller 110 (FIG. 1). At step 432, radiation is delivered to detector 104 (104') in accordance with the predetermined patient treatment, for example, via particle beam source 102. In some examples, operation of particle beam source 102 may be controlled via controller 110. Similar to FIG. 4A, during delivery of the radiation (step 432), current readout circuitry 106 may capture detector 104 (104') output, and provide a digitized output to particle analyzer 108. The digitized output may also be stored in storage 116. At step 434, the data acquisition cycle ends and the data acquisition is terminated, for example, by controller 110.

At step 436, the measured dose is compared to an expected dose for the predetermined patent treatment. For example, the measured dose may be determined by particle analyzer 108 (FIG. 1) and compared with an expected dose stored in storage 116, via controller 110.

If it is determined, at step 436, that the measured dose is not equal to the expected dose, step 436 proceeds to step 438. At step 420, possible causes for the measured dose not matching the expected dose are determined, and solutions for achieving the expected dose are identified. System 100 may be adjusted according to step 438, and step 438 proceeds to step 430. In some examples, if no solution is identified at step 438, the patient treatment may not be approved for delivery.

If it is determined, at step 436, that the measured dose is equal to the expected dose, step 436 proceeds to step 440. At step 440, it is determined, for example, by controller 110, that the patient treatment is approved for delivery.

FIG. 4C is a flowchart of an exemplary method for particle dose imaging for radiation delivery research and development. At step 442, steps 402-408 (FIG. 4A) are repeated. At step 444, predetermined gain settings for radiation delivery testing are provided to system 100. For example, the gain settings may be provided to system 100 by a user via user interface 112 (FIG. 1). In some examples, the predetermined gain settings may be stored in storage 116.

At step 446, a data acquisition cycle is initiated, for example, by controller 110 (FIG. 1). At step 448, radiation is delivered to detector 104 (104') in accordance with the gains settings for radiation delivery testing, for example, via particle beam source 102. In some examples, operation of particle beam source 102 may be controlled via controller 110. During delivery of the radiation (step 448), current readout circuitry 106 may capture detector 104 (104') output, and provide a digitized output to particle analyzer 108. The digitized output may also be stored in storage 116. At step 450, the data acquisition cycle ends and the data acquisition is terminated, for example, by controller 110.

At step 452, the measured data is analyzed, for example, by particle analyzer 108 (FIG. 1) and or controller 110. At step 454, the beam delivery components of system 100 may be adjusted, to attempt to improve the radiation delivery (i.e., to detector 104 (104')). Step 454 may proceed to step 446 and steps 446-454 may be repeated, to improve the radiation delivery.

FIG. 4D is a flowchart of an exemplary method for particle dose imaging for active beam monitoring with feedback to radiation delivery. At step 456, a patient is positioned on a treatment couch. At step 458, detector 104 (104') is positioned in the radiation beam line (to be directed to the patient positioned at step 456). At step 460, steps 404-408 (FIG. 4A) are repeated. At step 462, predetermined gain settings for radiation delivery are provided to system 100. For example, the gain settings may be provided to system 100 by a user via user interface 112 (FIG. 1). In some examples, the predetermined gain settings may be stored in storage 116.

At step 464, a data acquisition cycle is initiated, for example, by controller 110 (FIG. 1). At step 466, particle beam source 102 (FIG. 1) is activated and a radiation beam is delivered to the patient and to detector 104 (104'). The radiation is delivered in accordance with the gain parameters (step 462). In some examples, operation of particle beam source 102 may be controlled via controller 110.

At step 468, an image of the radiation beam is acquired by detector 104 (104'). Current readout circuitry 106 may convert the detector 104 (104') output to a digitized image. At step 470, one or more beam quality specifier(s) are determined from the acquired image, via particle analyzer 108 and/or controller 110. The digitized output and/or the beam quality specifier(s) may also be stored in storage 116. The specifier may include, without being limited to, a radiation beam position, a radiation beam arrival time, a radiation beam momentum and/or radiation beam dose distribution.

At step 472, it is determined whether the specifier(s) are within a predetermined tolerance, for example, by controller 110 (FIG. 1). If it is determined, at step 472, that the specifier(s) are within the predetermined tolerance, step 472 proceeds to step 468, and the process of acquiring an image and monitoring beam quality (steps 468-472) during radiation delivery (step 466) continues. For example, tolerances for the specifier(s) may be selected to ensure that the dose delivered to the patient is assured to be 1% or better. For this example, the beam position includes an accuracy of better than 1 mm, a beam arrival time better than 100 ms, a beam momentum better than 0.4 MeV and a beam dose distribution better than 2% (with respect to beam symmetry and flatness characteristics).

If it determined, at step 472, that the specifier(s) are not within the predetermined tolerance, step 472 proceeds to step 474. At step 474, it is determined (for example by controller 110) whether the system 100 parameters and/or delivery parameters of particle beam source 102 can be adjusted.

If it is determined, at step 474, that the system/delivery parameters can be adjusted, step 474 proceeds to step 476. At step 476, one or more system parameters and/or delivery parameters are adjusted, and step 476 proceeds to step 468. At step 468, the process of acquiring an image and monitoring beam quality (steps 468-472) during radiation delivery (step 466) continues.

If it is determined, at step 474, that the system/delivery parameter(s) cannot be adjusted (for example, by controller 110), step 474 proceeds to step 478, and the radiation delivery is aborted. For example, one or more system/delivery parameter(s) may be outside of a clinical safety tolerance range. This can occur due to mechanical issues, hardware issues and/or software issues, as discussed above.

FIGS. 5A-5D are example image frames illustrating particle beam position over a period of time determined based on particle therapy system 100 (FIG. 1). In particular, FIGS. 5A-5D illustrating four image frames from the Micromegas-based detector 104 demonstrating the time resolution of the system. Each square represents a 5 mm×5 mm pixel on the anode. The vertical and intensity scales indicate the current on each pixel, with zero meaning little or no current and one indicating maximum current scale that is observed when the radiation beam directly hits a group of pixels. In FIGS. 5A-5D, the current signal is converted to voltage (V) by preamplifiers 304 for digitization by ADC 306.

In FIGS. 5A-5D a proton beam is scanned in a left to right direction. The delivery is the modulated scanning technique, which is a step-and-shoot style in an ion beam application (IBA) system. The beam is delivered to points on a grid spaced by 2 mm. Each time point (frame) is a single dose point on that grid. The beam moves 2 mm between frame 1 (504 ms) (FIG. 5A) and 2 (512 ms) (FIG. 5B), another 2 mm for frame 3 (521.6) (FIG. 5C) and another 2 mm step for frame 4 (528.0 ms) (FIG. 5D). The beam is turned off when it is moved, which is resolved by the device in additional sub-frames (not shown). The sampling period for the examples of FIGS. 5A-5D was 1.6 ms.

The present invention is illustrated by reference to two examples. The examples are included to more clearly demonstrate the overall nature of the invention. The examples are exemplary, and not restrictive of the invention.

EXAMPLE 1

A prototype Micromegas chamber 600 (also referred to herein as Micromegas detector 600) with a segmented anode (i.e., an example of a Micromegas detector 104 as shown in FIG. 2A) was designed and assembled. The micromesh 602 (also referred to herein as mesh 602) and anode layer 604 were fabricated following a bulk Micromegas process. FIG. 6 illustrates a portion of the Micromegas chamber 600. The five readout anodes (of anode layer 604) can be seen in the center and are labeled 1-5. The woven micromesh 602 is held above the readout anodes 1-5 by photo-etched Kapton standoffs (visible as small points covering the anode plane) that maintain a uniform 128 μm gap. The center channel 5 of anode layer 604 is 5 cm in diameter. Also visible is the insulating ring, O-ring for gas seal, high voltage lead (lower right), and gas feed pipe (upper left).

The anode layer 604 of chamber 600 has a circular center channel 5 and four peripheral quadrants 1-4 (see FIG. 6) etched on one side of a standard 2 oz. double-sided copper clad G10 printed circuit board (PCB). The segments 1-5 are electrically connected to readout channels by plate-through holes to the back of the PCB. The micromesh 602 is a woven stainless steel mesh of 20 μm wires at 80 μm spacing. The micromesh 602 is held above the anode segments with a uniform gap (e.g., amplification gap 218 in FIG. 2A) of 128 μm by photo-etched standoffs. The micromesh 602 is connected to a high voltage feed by a copper trace on the PCB. The drift gap region (e.g., drift gap 214 in FIG. 2A) of 1.275 cm thickness is defined by a ring fabricated from polyether ether ketone (PEEK) insulator material that also has provisions for the gas inlet and outlet and gas seal o-rings. The drift cathode (not shown in FIG. 6 but shown as cathode 204 in FIG. 2A) is another G10 PCB. The chamber 600 uses a 70% argon, 30% CO2 gas mixture, selected to give lower gain but higher current capability. The Micromegas assembly contains an $^{55}$Fe (Iron-55) calibration source embedded in the drift region.

Figure 7B:
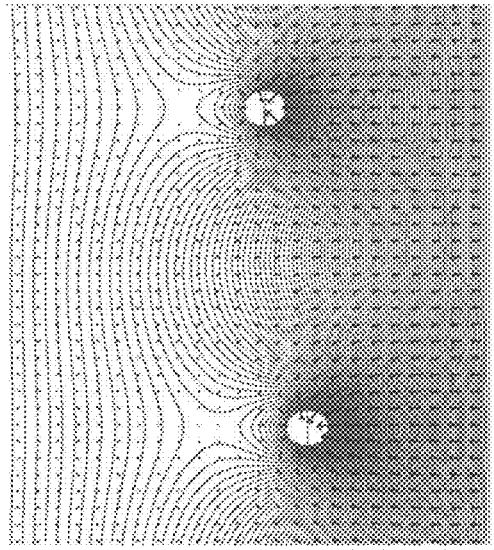
FIGS. 7A and 7B are example electromagnetic field simulations of an example Micromegas detector with the micromesh at positive or negative potential, respectively, according to an embodiment of the present invention.
Figure 7A:
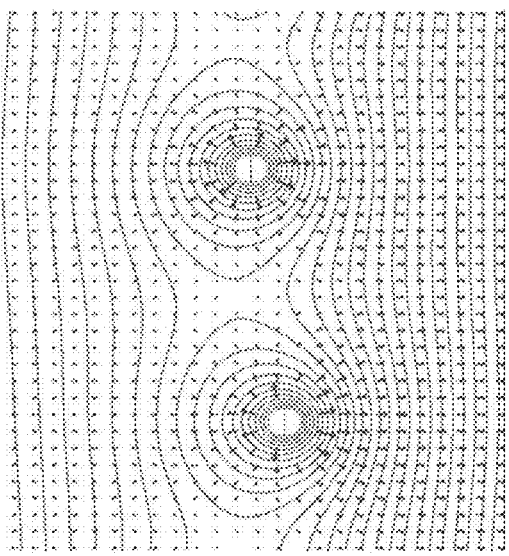

Typical operating potentials are −710V on the drift electrode and between −400 and −600V on the micromesh, depending on the desired gain. The choice of negative polarity for the mesh was guided by Poisson Superfish electromagnetic field simulations of the chamber geometry, as shown in FIGS. 7A and 7B. FIGS. 7A and 7B illustrate electromagnetic field simulations of the Micromegas geometry using Poisson Superfish with the micromesh held positive (FIG. 7A) or negative (FIG. 7B) relative to the electrode at the bottom of the plots.

In the case of the mesh held at negative potential relative to the collecting electrode, a high field region is created in the relatively narrow amplification gap between the mesh and the anode where gas gain occurs. The shape of the field near the mesh is such that it tends to focus electrons between the wires of the mesh as they move from the drift gap into the amplification region. Since the amplification occurs in the small gap region, positive ions can be cleared out more quickly.

Alternatively, the configuration with the mesh held positive relative to the electrodes is more like a multiwire proportional counter, with the electrons being collected at the mesh. Ionization gain occurs near the mesh wires where the field strength is very high, proportional to $\log(r_{wire}/r)$. Some gain is also realized in the amplification gap for primary ionization produced there; however, primary electrons from the drift region do not generally cross the mesh plane and the number of primary ions produced is small. A drawback of this configuration at high current is that slowly drifting positive ions produced near the mesh wires tend to build up in the low field regions that can be seen around the mesh wires in FIG. 7A. A buildup of positive ions near the mesh wires has the effect of increasing the effective wire diameter, $r_{wire}$, and so this type of chamber generally has less gain as beam current increases.

Based on measurements in proton beams of the gain using the two polarities, it was determined that the mesh held negative gives the ability to produce higher gains and that the gain is more stable with respect to variations in the beam current. There are also low field regions in the configuration with the mesh negative, but they tend to be located just above the mesh wires in the drift gap, where an accumulation of positive space charge may tend to defocus electrons drifting into the amplification region. However, the gain of the device is observed to be more stable.

FIG. 8A is a schematic showing the layout of an example preamplifier board used with the Micromegas chamber 600 (FIG. 6). The preamplifier board illustrated in FIG. 8A represents an example of current readout circuitry 106 shown in FIG. 3. The power module (top) is supplied with ±6 V by ribbon cable and provides power to the 10 amplifier modules. Ribbon connectors are used to connect the chamber channels (left) and the ADC data acquisition module (right). The preamp dimensions are indicated in inches. The chamber channels are connected at left and the data acquisition module interfaces with the ribbon connectors at right.

The preamplifier board was designed for the readout of ionization current on each of the five channels (FIG. 8A). Each preamplifier board has a total of ten channels. The power module derives stabilized ±5 V from an external power supply and an additional −1 V reference voltage to which the current through the input stage is compared. The current is fed into an operational amplifier and each channel supports two different gain settings individually selectable via an external digital input/output (I/O) bit to achieve a wider dynamic range. The relative high/low gain settings were selected to accommodate the different beam intensity produced by double-scattered and modulated-scanned delivery methods. The net gain of the overall system can be changed in several ways: there is a factor of 5 available in the digitizer gain, a factor of 40 in the high/low amplifier setting, and a factor of 200 in the gas gain for the micromesh voltage range under consideration. Additional adjustments can be accomplished with different gas choices.

The analog outputs from the amplifiers are connected to a DATAQ DI-720 (DATAQ Instruments, Akron, Ohio) which was configured to sample each channel at 1 kHz. The signals are digitized, serialized, and transferred to a PC connected to the DATAQ by Ethernet. Each channel is read at a 1 ms sampling interval for the experiments described here, though faster rates are possible.

The chamber assembly was irradiated with beams of protons at the Roberts Proton Therapy Center at the University of Pennsylvania. The cyclotron and beamline were designed by and are operated by ion beam applications (IBAs). The facility was designed to deliver therapeutic beams of up to 230 MeV protons to five treatment rooms using three different delivery techniques.

The first technique uses a double-scattered beam and is the least intense in terms of instantaneous dose (ionization) rate. Beamline components spread the beam to the maximum treatment field size (~20 cm) and then collimate to a target-specific treatment area using a Varian multileaf collimator (MLC) (Varian Medical Systems, Palo Alto, Calif.) comprised of 100 motorized tungsten leaves. The second type of beam is the uniform scanned beam, which is also collimated with the MLC, but the beam is magnetically scanned behind the collimator to generate larger field sizes. This delivery technique produces higher instantaneous dose rates at the time the beam is swept across the measurement volume. Finally, modulated-scanned beams, which are magnetically scanned only and not collimated, are finely focused with additional quadrupole magnets and are the most intense. Results presented herein were obtained using the double-scattered and uniform-scanning delivery techniques.

The beam range, defined as the water-equivalent depth at which the dose is 90% of the peak, that was used for these experiments was 17.5 cm, corresponding to a mean kinetic proton energy of about 170 MeV. The beam current at cyclotron extraction was 3 nA. The transport efficiency to the treatment rooms is nominally of order 10% at this beam energy. For some experiments, spread-out Bragg peaks (SOBPs) were delivered which are modulated using a range modulator wheel. SOBPs of 10 cm modulation (i.e., the length of the flat, high-dose part of the SOBP in the depth direction) were used. In other experiments, a single Bragg peak was delivered by stopping the modulator wheel on a particular segment. The MLC was used to collimate to small fields by opening a single leaf pair. The effective leaf width is 4.5 mm and the leaf pair was opened between 1 and 5 mm.

The entire chamber assembly was placed in a Faraday cage of 1/16 inch copper sheet for noise shielding and the Faraday cage was placed on top of the treatment couch near the isocenter position for the treatment room. An additional ionization chamber, composed of two sheets of copper clad G10, was located on top of the Faraday cage, upstream of the Micromegas chamber.

For the spread out and single Bragg peak measurements, an acrylic tank of dimensions 12 cm×12 cm transverse×30 cm depth was placed on top of the ionization chamber and filled with water. A drain pipe was used to siphon water from the tank at a controlled rate and data was collected continuously with the proton beam on while water flowed out of the tank. The total water-equivalent depth of the acrylic tank bottom, the ionization chamber, the top copper sheet of the Faraday cage, and the cathode G10 board of the Micromegas chamber is calculated to be 2.2 cm using stopping power ratios to water from the NIST PSTAR database for 170 MeV protons.

Beam transverse profiles were measured with Gafchromic EBT2 film. A calibration curve was constructed for this batch of film by delivering uniform dose cubes of varying total number of MUs with the film located in the center of the delivered dose. The film was scanned and digitized with an Epson 10000XL flatbed scanner. The red color channel was used for the optical density measurement.

Some of the Micromegas chamber measurements are compared to Monte Carlo results generated using simulation code developed at the University of Pennsylvania for the IBA proton therapy nozzles and Varian MLC using the Geant4 version 9.4 (Patch-01) toolkit. The modulator wheels are implemented based on IBA specification and the beam current modulation is optimized using least-squares fitting in order to reproduce commissioning measurements. The simulations reproduce the beam range to within 2 mm and 1% dose accuracy everywhere for both the double-scattering and uniform-scanning modalities.

Figure 9:
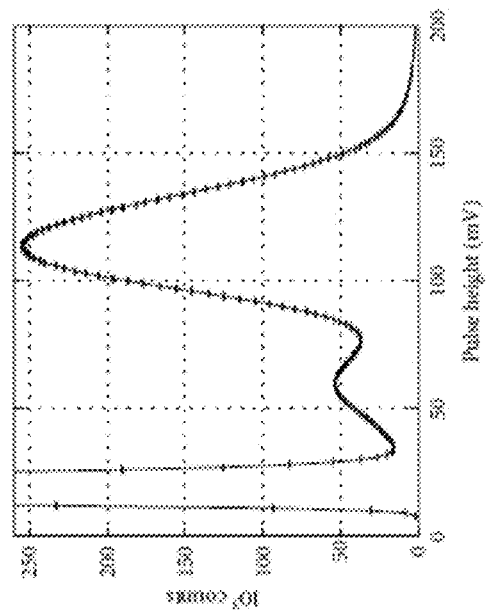
FIG. 9 is a graph of average of current pulses from a test source and calibration signal through a shaping amplifier for an exemplary particle therapy system, according to an embodiment of the present invention.
Figure 10:
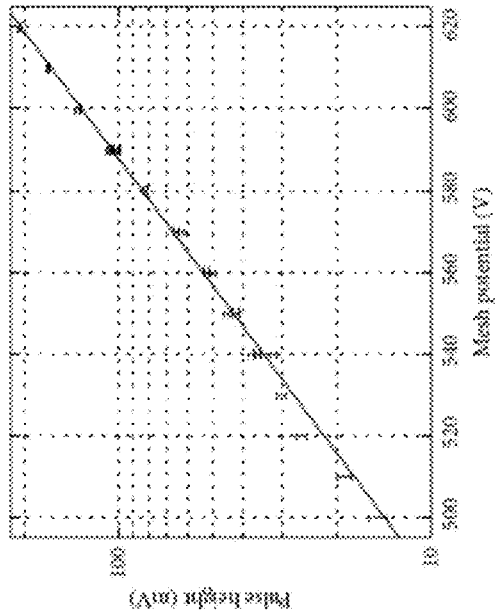
FIG. 10 is a graph of calibration pulse height distribution for an exemplary particle therapy system, according to an embodiment of the present invention.
Figure 11:
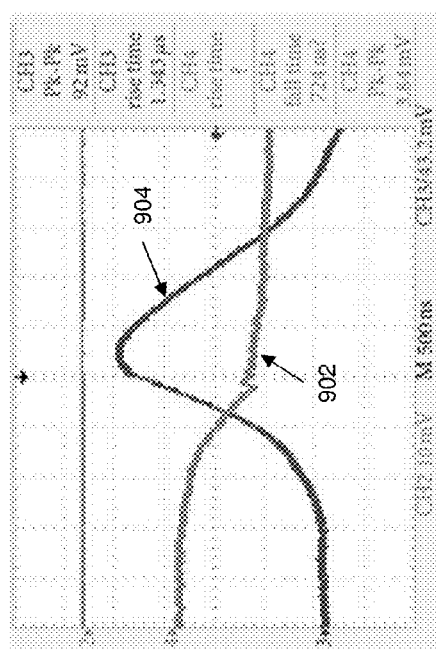
FIG. 11 is a graph of pulse height as a function of pressure for an exemplary particle therapy system, according to an embodiment of the present invention.
Figure 12:
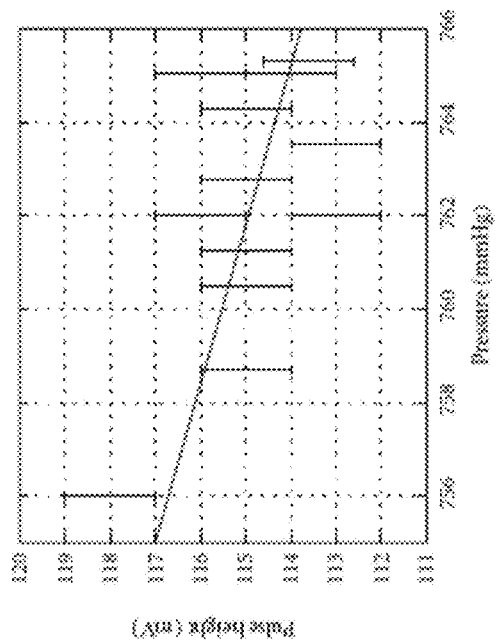
FIG. 12 is a graph of pulse height as a function of mesh potential for an exemplary particle therapy system, according to an embodiment of the present invention.

FIG. 9 is a graph of average of current pulses from a $^{55}$Fe test source (trace 902) and the calibration signal through a shaping amplifier (trace 904). FIG. 10 is a graph of an example of calibration pulse height distribution from the $^{55}$Fe calibration source embedded in the Micromegas chamber with mesh at −590 V. The pulse height is strongly dependent on the mesh potential, and somewhat dependent on the ambient temperature and pressure. The position of the main peak is used as a daily gain calibration for the Micromegas. The smaller peak is the Argon escape peak. FIG. 11 is a graph of a pulse height versus pressure with a $^{55}$Fe calibration source for a −590 V mesh. FIG. 12 is a gain calibration curve for the Micromegas chamber as a function of mesh potential.

The chamber gas and gain calibration uses a readout connected to the mesh. Typical pulses from the source are shown in FIG. 9. The pulse height spectrum of the $^{55}$Fe calibration (FIG. 10) can be used to correct for variations in the absolute gain due to changes in gas, voltage, temperature, or pressure since it measures the absolute gain. FIG. 11 shows the peak height for −590 Vmesh as a function of pressure and indicates that gain corrections for pressure and temperature are of the order of a few percent. The gas gain as a function of mesh voltage is given in FIG. 12.

Figure 13:
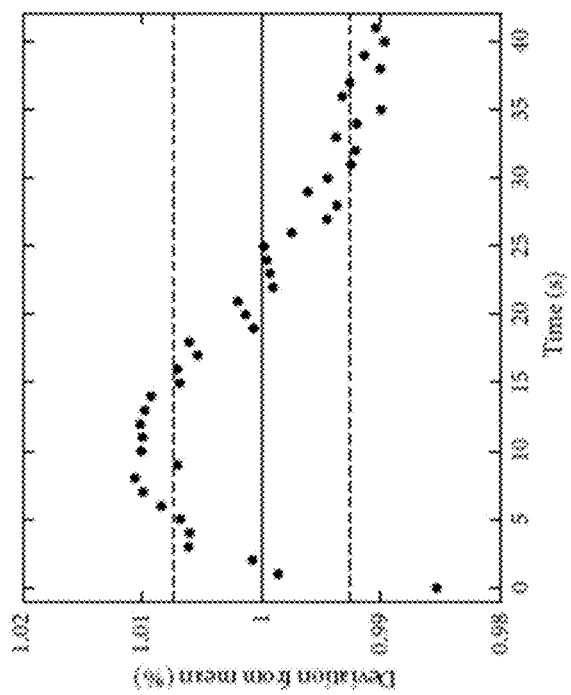
FIG. 13 is a graph of deviation from mean response as a function of time illustrating a reproducibility of a Micromegas detector response for an exemplary particle therapy system, according to an embodiment of the present invention.

For proton therapy applications, one is typically interested in the total dose delivered to a spatial region. It is desirable for the integral response of the chamber to be very stable across a wide dynamic range. The precision of the integrated Micromegas chamber signal was measured by assuming a constant beam current and delivering the proton beam to the chamber for one second intervals. For each of 42 one second beam deliveries, the total charge collected by the center channel was determined by integrating the digitized signal. FIG. 13 shows the results of those irradiations.

FIG. 13 is a graph illustrating the reproducibility of the chamber response in the proton beam. The detector was irradiated in one-second intervals. The integrated response of the chamber is constant across the 42 measurements to 0.8% (1σ). The signal fluctuates on about a one-minute timescale and is likely due to a drift in the beam current. The standard deviation from the mean for these 42 measurements is 0.8%. The data show a remarkable drift in time with a timescale of about one minute. It is believed that it is the beam current that is fluctuating and not the chamber response, and consider this value to be an upper limit on the chamber precision.

Figure 14:
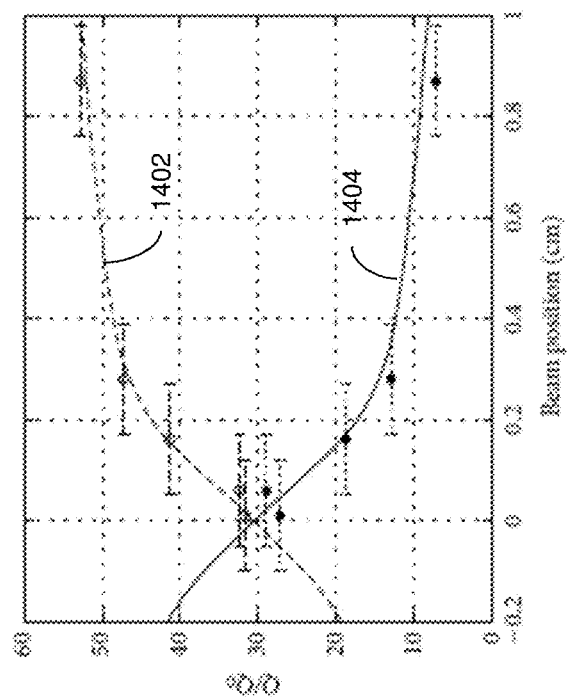
FIG. 14 is a graph of spatial resolution measurements as a function of beam position for an exemplary particle therapy system, according to an embodiment of the present invention.

The spatial resolution of the Micromegas chamber is measured by moving the chamber with the treatment couch across a uniform-scanned beam collimated with a 4 mm×4.5 mm aperture positioned near the boundary between channels 2 and 5. FIG. 14 is a graph illustrating the spatial resolution measurement for the Micromegas chamber using a beam moving across the boundary between channels 2 and 5. The lines represent the fraction of the integrated beam profile that is delivered to channel 2 (dotted line 1402) and channel 5 (solid line 1404). The data points are the integrated charge Q measured on the given channel relative to the charge $Q_0$ measured with the transmission ionization chamber in the delivery nozzle. The ratio of the signal on the two channels can be used as a beam position measurement with σ=1.1 mm.

The profile of this beam was determined at the elevation of the center of the Micromegas drift gap by placing a piece of Gafchromic EBT2 film downstream of the chamber PCBs and the Faraday cage top plate. The beam is sufficiently narrow (4.3 mm FWHM) in the direction transverse to the direction of couch travel such that all charge is collected on channels 2 and 5. A ratio of the signal on channel 2 to the signal on channel 5 provides a position measurement for the beam. As discussed above, σ=1.1 mm was measured for the beam position measurement using the Micromegas chamber.

The double-scattered proton beam delivery technique uses a modulator wheel with segments of varying thicknesses of Lexan and Pb to produce a flat spread-out Bragg peak (SOBP). The wheel rotates at a nominal 10 Hz and the beam is pulsed in phase with the wheel. The number of segments irradiated determines the length of the flat part of the SOBP in the depth direction. The Micromegas signal in this type of beam is shown in FIGS. 15A-15C.

FIG. 15A illustrates Micromegas measurement (black points) of a proton spread-out Bragg peak (SOBP) delivered using the double-scattered technique. Five individual Bragg peaks can be seen corresponding to the first (most distal) five segments on the modulator wheel. The five Bragg peaks combine to produce a flat SOBP, as shown by the line 1502, which was obtained by summing the Micromegas signal over three complete wheel rotations. Two regions are highlighted for closer examination: region (b) (shown in FIG. 15B) and region (c) (shown in FIG. 15C). FIG. 15B shows the series of pulses generated by the modulator wheel increasing in amplitude as the water depth lowers, effectively moving the detector into the distal falloff region. FIG. 15C shows three wheel rotations at a depth where four Bragg peaks can be discerned both in the datapoints in FIG. 15A and in the pulses in FIG. 15C.

The water level was lowered continuously with the beam on a rate of 0.14 mm/s. FIGS. 15B and 15C show that the Micromegas chamber can resolve the time structure of this delivery technique. Each pulse corresponds to a rotation of the modulator wheel. Four segments of the wheel can be identified in FIG. 15C, though the fourth gives a very low signal at the depth of the measurement (about 16.5 cm) and is in the beam for only a few ms before the next segment. In order to produce a flat SOBP, the relative weight of Bragg peaks are set by the angular width of the corresponding segment on the modulator wheel and fine-tuned by modulating the beam current in phase with the wheel rotation. FIGS. 15A-15C show that the sum of the measurements over the wheel rotation indeed produces a flat SOBP.

Figure 16:
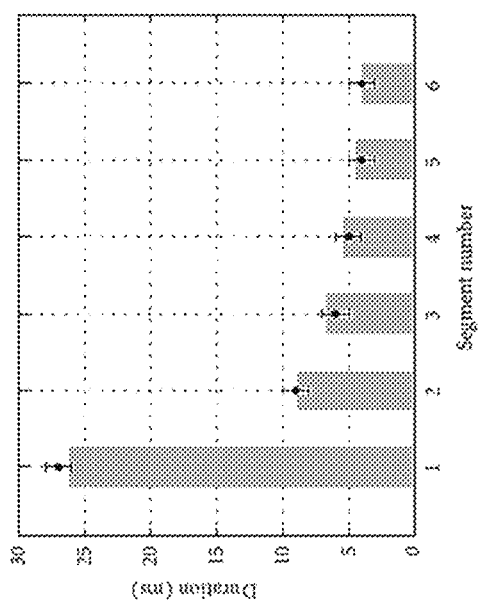
FIG. 16 is a graph of signal voltage as a function of time for pulses produced by a range modulator wheel at different depths in water for an exemplary particle therapy system, according to an embodiment of the present invention.

By smoothing individual pulses for amplifier response and then averaging over the ten pulses contained in one second of data at a particular depth, it is possible to construct profiles of the beam energy passing through the rotating wheel at different depths yielding detailed information about the wheel structure. Examples of these pulses at six different depths are shown in FIG. 16. FIG. 16 illustrates pulses produced by the range modulator wheel at six different depths in water averaged over one second intervals. In order of increasing width, the pulses were taken from the data in FIG. 15A at time 0 s, 51 s, 130 s, 190 s, and 237 s, corresponding to water-equivalent depths of 17.9 cm, 17.2 cm, 16.2 cm, 15.4 cm and 14.8 cm, respectively.

Figure 17:
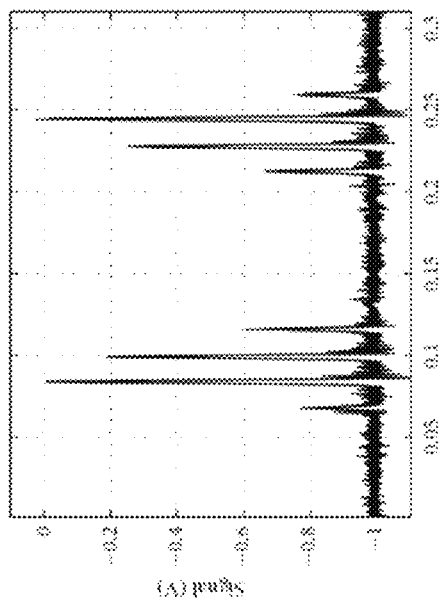
FIG. 17 is a bar graph of duration as a function of segment number during which segments of a modulator wheel cross a beam path for an exemplary particle therapy system, according to an embodiment of the present invention.

The leading and trailing edge of the distributions can be used to extract the size of the wheel angular segments and compare them to specifications from the manufacturer. Individual wheels may vary slightly and this technique is capable of measuring the differences between wheels in different treatment rooms. The comparison for the room used in these tests is shown in FIG. 17 and the agreement is excellent. FIG. 17 illustrates duration (in ms) during which segments of a modulator wheel cross the beam path measured with the Micromegas chamber 600 (points with error bars) compared to the manufacturer data (shaded columns). The measurements were extracted from the pulses at six different depths in water averaged over one second shown in FIG. 16.

Figure 18:
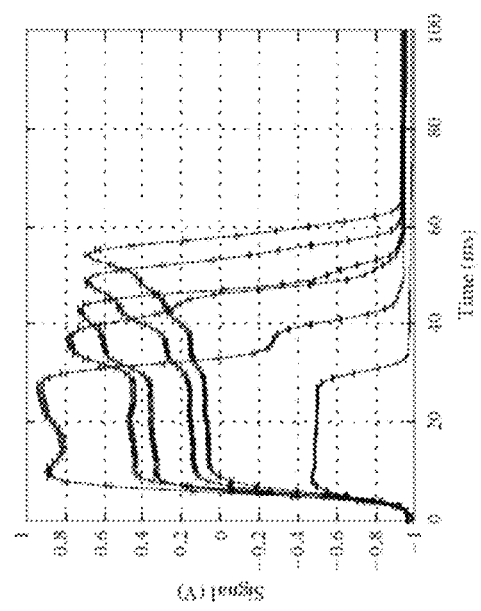
FIG. 18 is a graph of amplitude as a function of frequency for ionization current collected for an exemplary particle therapy system, according to an embodiment of the present invention.

A Fourier transform of the signal collected with the double-scattering delivery is shown in FIG. 18. FIG. 18 illustrates a Fourier transform of ionization current collected using the double-scattered proton delivery technique. This provides a measurement of the wheel angular frequency of 10.0046±0.0032 Hz.

Figure 19:
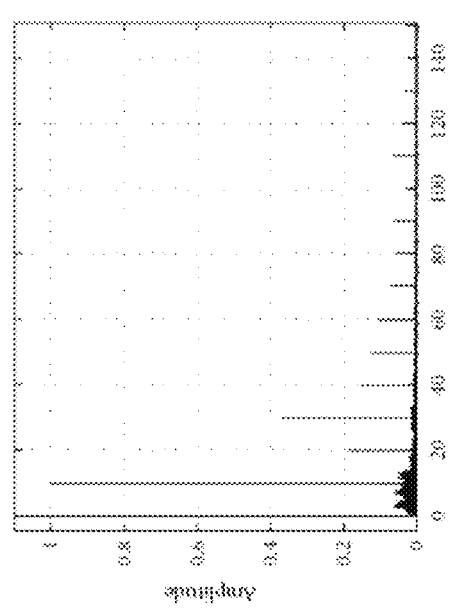
FIG. 19 is a graph of signal voltage as a function of time for an ionization signal collected using an exemplary particle therapy system, according to an embodiment of the present invention.
Figure 20:
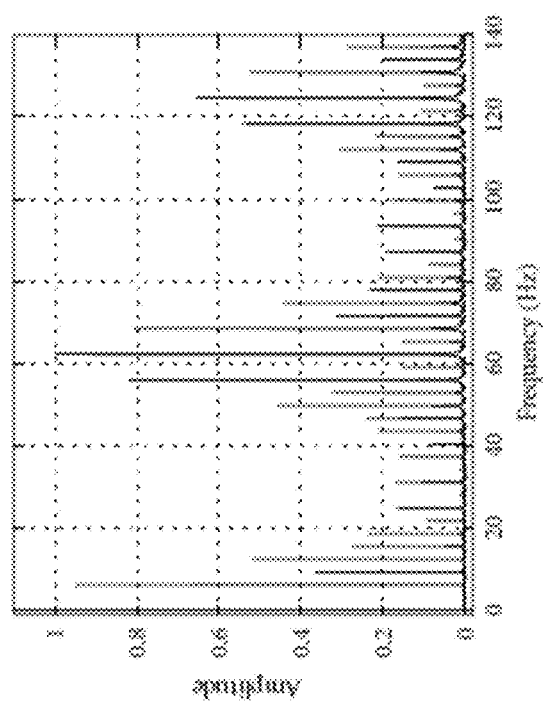
FIG. 20 is a graph of amplitude as a function of frequency of uniform-scanning delivery data for an exemplary particle therapy system, according to an embodiment of the present invention.

A uniform-scanned beam of 17.5 cm water equivalent proton range was collimated to 5 mm×4.5 mm using the MLC. The beam is scanned magnetically at nominal 3 Hz in the head to foot transverse direction and 30 Hz in the left right direction. FIG. 19 shows a typical signal in the center channel of the Micromegas chamber for this kind of delivery. FIG. 19 illustrates an ionization signal from the Micromegas chamber 600 (FIG. 6) using the uniform-scanned proton delivery technique in which a relatively large Gaussian spot is magnetically scanned to produce a large, uniform fluence behind a collimating aperture. The aperture was 5 mm×4.5 mm. The beam was on for 21 seconds and 65 pairs of pulse sets were collected in that time. All 65 sets are plotted here by shifting the phase of each set by 0.32112 s. FIG. 20 illustrates a Fourier transform of uniform-scanning delivery data. The fundamental frequencies are measured as 6.2291 Hz and 62.29 Hz. The beam scanning frequencies are one-half these values, because the beam passes the collimator hole twice per scan cycle.

In FIG. 19, each peak arises from the beam scanning at the high frequency across the collimation hole. The first four peaks correspond to the beam moving slowly in the head-to-foot direction. The pattern is reversed as the beam is scanned back in the opposite direction. The pattern of pulses observed is consistent with the nominal frequency values, but illustrates that much more accurate measurements are possible. In particular, from the Fourier transform of this data (FIG. 20) measurements of the scanning frequencies are: 3.1146 Hz±0.2% in the slow direction, and 31.146 Hz±0.04% in the fast direction (using the fundamental peaks).

However, FIG. 20 is actually 65 consecutive pulse patterns plotted with a phase shift of 0.32112 s between pulses. The 65 pulse trains overlay extremely well indicating that the beam scan pattern is very well controlled and reproducible. Changing the phase shift by only 0.00001 s disrupts the overlay of the pulses, and so this is a measurement of one of the scan frequencies which is much more precise than that from the Fourier transform: 3.1141 Hz±0.002%. At this level of precision one has to consider the accuracy of the data acquisition clock itself.

A pristine (unmodulated) Bragg peak was delivered to the detector by stopping the modulator wheel on the first (thinnest) segment. The beam was collimated with a 5 mm×4.5 mm aperture. The beam was not scanned. The water level was lowered continuously with the beam on at a rate of 0.14 mm/s. The data collected with the Micromegas chamber 600 is compared with Geant4 simulations in FIG. 21.

Figure 21:
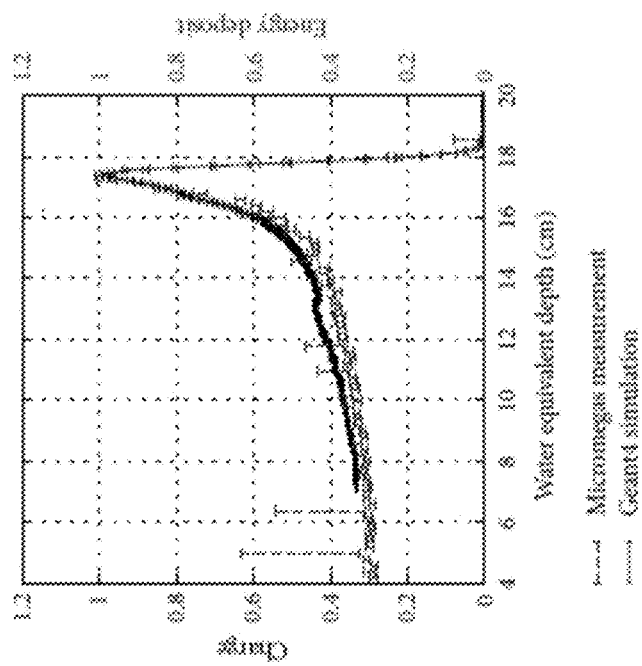
FIG. 21 is a graph of charge as a function of water depth for a proton Bragg measurement using an exemplary particle therapy system of the present invention and for a simulation.

FIG. 21 illustrates a proton Bragg peak measurement using the Micromegas chamber 600 compared with Geant4 simulation of the IBA Universal Nozzle, Varian MLC, and the Micromegas detector and water column. Agreement is within 5% across the water-equivalent depth range from 7.5 cm-19.5 cm. The curves are normalized at the peaks. The error bars on the Micromegas measurement represent the 0.8% dose reproducibility (see FIG. 13) and the error bars on the simulation represent the Monte Carlo sample variance.

The measured detector signals indicate that the beam in this configuration is synched to 60 Hz and is on for 10.00 microseconds and off for the following 6.67 microseconds. Averaging samples over as few as 10 pulses (1 second) can be used to detect pulse-to-pulse variations in delivered current to high accuracy, as shown in FIG. 16 which shows the result of averaging 5 pulses to the left and 5 to the right and the effect of smoothing the distribution. The result is a fraction of a percent accuracy every second.

There are over two orders of magnitude difference in the instantaneous ionization rates encountered in proton therapy, from the relatively low rate double-scattered delivery to the high-rate modulated-scanning delivery, with uniform-scanning intermediate between the other two. The exemplary Micromegas chamber described herein is designed to resolve typical treatment dose rates for all modalities and is capable of a very wide dynamic range. In the example, the digitization gain is adjustable, each channel of the preamplifier board has two gain settings switchable by external digital control and further fine tuning of the gain may be accomplished by adjusting the mesh potential using a calibration curve like that shown in FIG. 12 and remeasuring the gain with the calibration channel.

The measurements indicate the Micromegas response is reproducible to better than 0.8% in a double-scattered proton therapy beam. Indeed, while ionization chambers are currently the standard for absolute dosimetry in the field of external beam therapy, the exemplary Micromegas detectors described herein may achieve the same absolute level of accuracy with vastly improved spatial and time resolutions.

It is desirable for an exemplary Micromegas detector 104 (FIG. 1) to achieve stable gain, including a precise method to correct for ambient conditions. This may be achieved by a feedback voltage of order less than 1 volt applied to the preamp voltage reference and calibrated using the calibration source.

In the above example, the data resolve the very stable uniform scanning pattern (FIG. 19) and therefore provides a measurement of the unknown beam profile upstream of the collimator. The peak of each pulse in FIG. 19 corresponds to a point on the (Gaussian) beam profile in the slow scanning direction, or more precisely, the beam profile convolved against the aperture window. Furthermore, the width of these pulses determines the scan velocity of the beam in the fast scan direction, given the size of the aperture in that dimension.

EXAMPLE 2

Current linear accelerators offer very high photon dose rates (e.g., greater than or equal to about 1,000 MU/min) that can shorten patient treatment time. High dose rates, however, can present a challenge for real-time monitoring of the treatment beam, because of dose rate effects encountered with standard detector technologies. An example dose rate effect for gas-based chambers includes ion recombination. The unique field-shaping provided by exemplary Micromegas detectors 104, 104' and 600 (i.e., when the micromesh is held at negative potential relative to the collecting electrode) allows for a fast clearing of slow-moving positive ions that minimizes the recombination effect.

To demonstrate the suitability of exemplary Micromegas detectors for high dose rate photon beam monitoring and dosimetry applications, photon beams were delivered to Micromegas detector 600 (described above with respect to FIG. 6) at different dose rates. The photon beams were delivered using a Varian TrueBeam linear accelerator (Varian Medical Systems, Palo Alto, Calif.) in 6 MV flattening filter free mode). The Varian TrueBeam linear accelerator currently offers the highest dose rates available for therapy.

Figure 22:
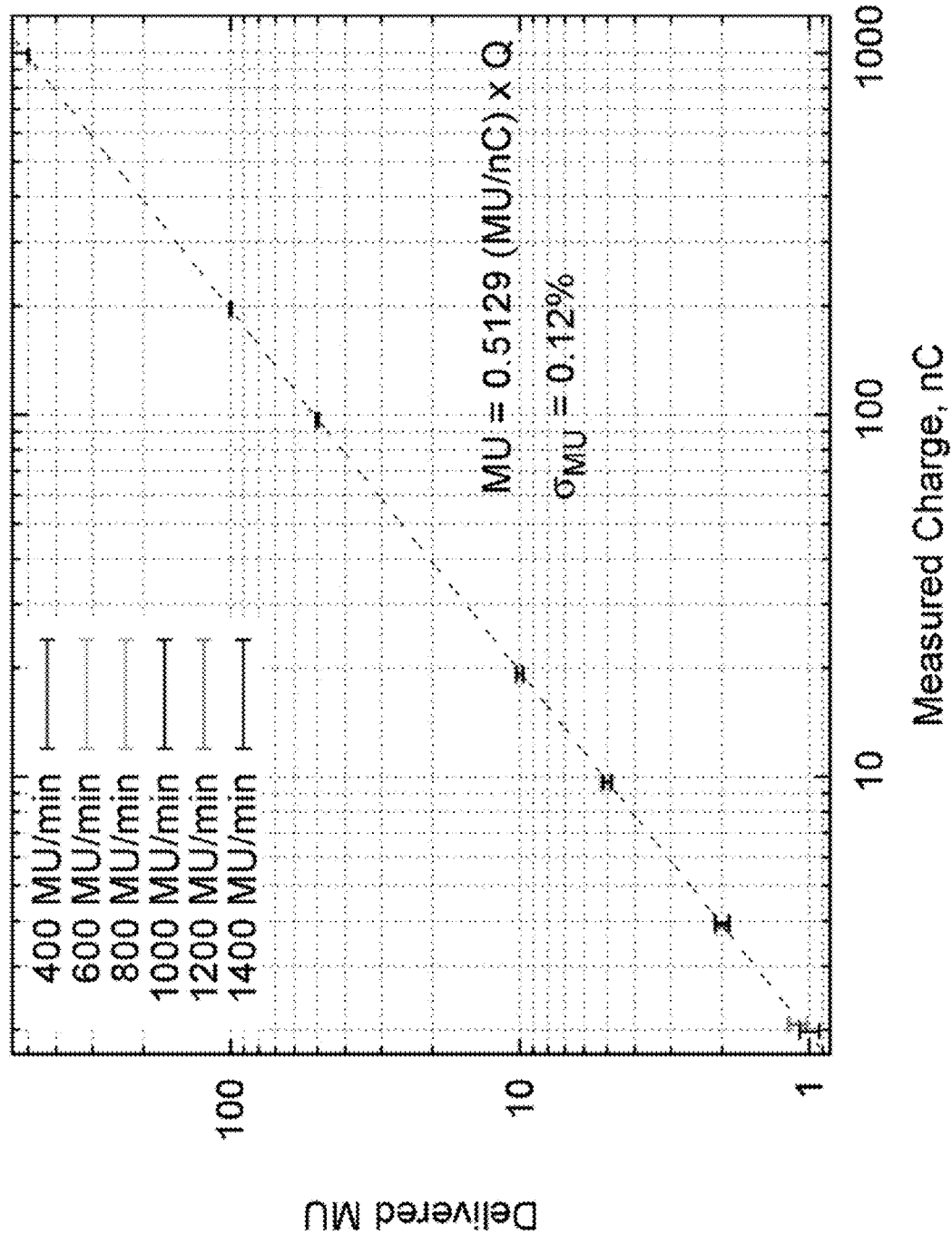
FIG. 22 is a graph of delivered monitor unit (MU) as a function of measured charge for a photon beam delivered at different dose rates to an exemplary Micromegas detector of the present invention.

FIG. 22 is a graph of delivered MU as a function of measured charge for a photon beam delivered at different dose rates to exemplary Micromegas detector 600. The dose rates include 400 MU/min, 600 MU/min, 800 MU/min, 1000 MU/min, 1200 MU/min and 1400 MU/min. Particle therapy system 100 (which includes Micromegas detector 600) is calibrated such that 1 MU delivers a dose of 1 cGy at the depth of dose maximum under the reference condition that is a 10 cm×10 cm field size and a source-to-surface distance of 100 cm.

FIG. 22 shows a precise charge-to-MU calibration (Q) with essentially no dose rate dependence. The precision of the calibration ($\sigma_{MU}$) is 0.12% (in contrast to current chambers that are about 1%), which is averaged over all dose rates (varied more than a factor of 3) and over three orders of magnitude with respect to delivered MU. FIG. 22 indicates that exemplary Micromegas detectors (e.g., 104, 104', 600) perform very well in photon beams (as well as in proton beams, as indicated above with respect to Example 1). The graph of FIG. 2 demonstrates no observable difference in detector response as a function of dose rate, indicating that the detector operates in a regime where recombination is not an issue.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A particle therapy system comprising:
    a particle therapy beam source for generating a particle therapy beam the particle therapy beam including particles selected from the group consisting of protons and positive ions;
    a plurality of particle detectors at least partially overlapping one another in a stacked configuration and configured to detect the particle therapy beam, each particle detector including an ionization chamber configured to receive a gas, a mesh electrode, at least one anode, and an amplification gap between the mesh electrode and the at least one anode, wherein one or more of a size of the amplification gap, a composition of the gas, or a gain of one or more of the plurality of particle detectors enables a linear response of the one or more particle detectors for a 2 Gray dose to a one liter volume delivered by the particle therapy beam within about two minutes or less; and
    an analyzer configured to generate a three-dimensional representation of the particle therapy beam based on the detection of the particle therapy beam by at least a portion of the plurality of particle detectors in the stacked configuration.

2. The system of claim 1, each of the plurality of particle detectors includes a Micromesh Gaseous Structure (Micromegas) detector, and wherein the gain has an order of magnitude of a hundred.

3. The system of claim 1, further comprising readout circuitry, the readout circuitry including at least one preamplifier to amplify a charge from the plurality of particle generators to form an amplified signal.

4. The system of claim 1, wherein the particle therapy apparatus modifies a characteristic of the particle therapy beam source responsive to one or more of the three-dimensional representation or a characterization result based on charge collected by the at least a portion of the plurality of particle detectors.

5. The system of claim 1, wherein the analyzer generates a characterization result based on the three-dimensional representation.

6. The system of claim 1, wherein each of the plurality of particle detectors includes:
    a cathode and the at least one anode, the charge being collected by the at least one anode, wherein the ionization chamber is disposed between the corresponding cathode and the at least one anode, and wherein the mesh electrode is disposed in the ionization chamber between the cathode and the at least one anode.

7. The system of claim 6, wherein a drift gap between the cathode and the mesh electrode has an order of magnitude of a centimeter.

8. The system of claim 6, wherein the amplification gap is between 100 µm to 1000 µm.

9. The system of claim 1, wherein the gas comprises a mixture of 70% argon +30% $CO_2$.

10. The system of claim 6, wherein the at least one anode includes a plurality of electrically conductive segments.

11. The system of claim 8, wherein the plurality of electrically conductive segments include a plurality of strips parallel to each other or a plurality of pixels in a checkerboard configuration.

12. A method for particle dose imaging, the method comprising:
    generating a particle therapy beam, the particle therapy beam including particles selected from the group consisting of protons and positive ions;
    directing the particle therapy beam to be incident on a plurality of particle detectors at least partially overlapping one another in a stacked configuration such that the plurality of particle detectors detect the particle therapy beam, each particle detector including an ionization chamber configured to receive a gas, a mesh electrode, at least one anode, and an amplification gap between the mesh electrode and the at least one anode, wherein one or more of a size of the amplification gap, a composition of the gas, or a gain of one or more of the plurality of particle detectors enables a linear response of the one or more particle detectors for a 2 Gray dose to a one liter volume delivered by the particle therapy beam within about two minutes or less; and
    generating a three-dimensional representation of a particle dose of the particle therapy beam based on detection of the particle therapy beam by at least a portion of the plurality of particle detectors in the stacked configuration.

13. The method of claim 12, wherein each particle detector includes a Micromesh Gaseous Structure (Micromegas) detector.

14. The method of claim 12, the method further comprising:
    generating a characterization result of the particle therapy beam based on one or more of the three-dimensional representation or a particle dose image of the particle therapy beam.

15. The method of claim 14, wherein the particle therapy beam is associated with a particle imaging application including at least one of a predetermined patient treatment test, a machine quality assurance test or a predetermined radiation delivery, the method further comprising:
    comparing the characterization result to a predetermined value associated with the particle imaging application to at least one of verify or monitor the particle imaging application.

16. A particle therapy system comprising:
    a particle therapy beam source for generating a particle therapy beam, the particle therapy beam including particles selected from the group consisting of protons and positive ions; and
    a plurality of particle detectors at least partially overlapping one another in a stacked configuration wherein each of the particle detectors comprise an ionization chamber configured to receive a gas, a mesh electrode, at least one anode, and an amplification gap between the mesh and the at least one anode, wherein one or more of a size of the amplification gap, a composition of the gas, or a gain of one or more the plurality particle detector enables the plurality of particle detectors to generate one or more signals for representing a three-dimensional dose distribution of the particle therapy beam for a 2 Gray dose to a one liter volume delivered by the particle therapy beam within about two minutes or less.

17. A method for particle dose imaging, the method comprising:
generating a particle therapy beam adapted, the particle therapy beam including particles selected from the group consisting of protons and positive ions; and
directing the particle therapy beam to be incident on at least one particle detector of a plurality of particle detectors at least partially overlapping one another in a stacked configuration, wherein each of the particle detectors comprise an ionization chamber comprising a gas, a mesh electrode, at least one anode, and an amplification gap between the mesh and the at least one anode, wherein one or more of a size of the amplification gap, a composition of the gas, or a gain of one or more the plurality particle detector enables the plurality of particle detectors to generate one or more signals for representing a three-dimensional dose distribution of the particle therapy beam for a 2 Gray dose to a one liter volume delivered by the particle therapy beam within about two minutes or less.

18. The system of claim 1, wherein each of the plurality of particle detectors have a gain of from 1 to 1000.

19. The system of claim 1, wherein the three-dimensional representation comprises a three-dimensional image.

20. The method of claim 12, further comprising:
integrating a charge collected by at least one channel of the plurality of particle detectors, wherein the three-dimensional representation is based on a result of integrating the charge.

* * * * *